United States Patent
Schinazi et al.

(10) Patent No.: US 6,245,749 B1
(45) Date of Patent: *Jun. 12, 2001

(54) NUCLEOSIDES WITH ANTI-HEPATITIS B VIRUS ACTIVITY

(75) Inventors: Raymond F. Schinazi, Decatur, GA (US); Jean-Pierre Sommadossi, Birmingham, AL (US); Gilles Gosselin; Jean-Louis Imbach, both of Montpellier (FR)

(73) Assignee: Emory University, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/112,878

(22) Filed: Jul. 9, 1998

Related U.S. Application Data

(63) Continuation of application No. 08/485,716, filed on Jun. 7, 1995, which is a continuation-in-part of application No. 08/320,461, filed on Oct. 7, 1994, now abandoned.

(51) Int. Cl.$^7$ .......................... A61K 31/70; C07H 19/16; C07H 19/20
(52) U.S. Cl. .................... 514/47; 536/26.7; 536/27.14
(58) Field of Search .................... 514/47; 536/26.7, 536/27.14

(56) References Cited

U.S. PATENT DOCUMENTS

| | | |
|---|---|---|
| 4,000,137 | 12/1976 | Dvonoch et al. |
| 4,140,761 | 2/1979 | Gerin et al. |
| 4,336,381 | 6/1982 | Nagata et al. |
| 4,818,538 | 4/1989 | Rideout et al. |
| 4,861,759 | 8/1989 | Mitsuya et al. |
| 4,879,277 | 11/1989 | Mitsuya et al. |
| 4,900,828 | 2/1990 | Belica et al. |
| 4,916,122 | 4/1990 | Chu et al. |
| 4,963,533 | 10/1990 | de Clercq et al. |
| 5,041,449 | 8/1991 | Belleau et al. |
| 5,047,407 | 9/1991 | Belleau et al. |
| 5,059,690 | 10/1991 | Zahler et al. |
| 5,089,500 | 2/1992 | Daluge. |
| 5,149,794 | 9/1992 | Yatvin et al. |
| 5,151,426 | 9/1992 | Belleau et al. |
| 5,179,104 | 1/1993 | Chu et al. |
| 5,185,437 | 2/1993 | Koszalka et al. |
| 5,194,654 | 3/1993 | Hostetler et al. |

(List continued on next page.)

FOREIGN PATENT DOCUMENTS

| | | |
|---|---|---|
| 0 217 580 | 4/1987 | (EP) . |
| 0 337 713 | 10/1989 | (EP) . |
| 0 433 898 | 12/1989 | (EP) . |
| 0 350 287 | 1/1990 | (EP) . |
| 0 375 329 | 6/1990 | (EP) . |
| 0 382 526 | 8/1990 | (EP) . |
| 0 494 119 | 7/1992 | (EP) . |
| 0 515 144 | 11/1992 | (EP) . |
| 0 515 156 | 11/1992 | (EP) . |
| 0 515 157 | 11/1992 | (EP) . |
| 0 526 253 | 2/1993 | (EP) . |
| WO 88/07532 | 10/1988 | (WO) . |
| WO 88/08001 | 10/1988 | (WO) . |
| WO 89/02733 | 4/1989 | (WO) . |
| WO 90/00555 | 1/1990 | (WO) . |
| WO 90/12023 | 10/1990 | (WO) . |
| WO 91/11186 | 8/1991 | (WO) . |
| WO 91/16920 | 11/1991 | (WO) . |
| WO 91/17159 | 11/1991 | (WO) . |
| WO 91/18914 | 12/1991 | (WO) . |
| WO 91/19721 | 12/1991 | (WO) . |
| WO 92/00315 | 1/1992 | (WO) . |
| WO 92/06102 | 4/1992 | (WO) . |
| WO 92/08717 | 5/1992 | (WO) . |
| WO 92/10496 | 6/1992 | (WO) . |
| WO 92/10497 | 6/1992 | (WO) . |
| WO 92/14729 | 9/1992 | (WO) . |
| WO 92/14743 | 9/1992 | (WO) . |
| WO 92/15308 | 9/1992 | (WO) . |
| WO 92/18517 | 10/1992 | (WO) . |
| WO 92/21676 | 12/1992 | (WO) . |
| WO 93/00910 | 1/1993 | (WO) . |
| WO 93/12128 | 6/1993 | (WO) . |
| WO 93/12131 | 6/1993 | (WO) . |
| WO 93/12132 | 6/1993 | (WO) . |
| WO 93/24510 | 12/1993 | (WO) . |
| WO 94/04154 | 3/1994 | (WO) . |
| WO 94/05300 | 3/1994 | (WO) . |
| WO 94/09793 | 5/1994 | (WO) . |
| WO 94/14456 | 7/1994 | (WO) . |
| WO 94/14802 | 7/1994 | (WO) . |
| WO 94/27616 | 7/1994 | (WO) . |
| WO 94/26273 | 11/1994 | (WO) . |
| WO 94/26764 | 11/1994 | (WO) . |
| WO 95/07086 | 3/1995 | (WO) . |
| WO 95/07287 | 3/1995 | (WO) . |
| WO 95/11252 | 4/1995 | (WO) . |
| WO 95/20595 | 8/1995 | (WO) . |
| WO 96/15132 | 5/1996 | (WO) . |
| WO 96/40164 | 12/1996 | (WO) . |

OTHER PUBLICATIONS

Ayoola, et al., "Progress in the Control of Viral Hepatitis: Memorandum from a WHO Meeting," *Bulletin of the World Health Organization*, 66(4):443–455 (1988).

Beach, J.W., et al., "Synthesis of EnantiomericallyPure (2'R,5'S)–(–)–1–[2–(hydroxymethyl)–oathiolan–5–yl]Cytosine . . . ," *J. Org. Chem.* 57:2217–2219 (1992).

(List continued on next page.)

Primary Examiner—James O. Wilson
Assistant Examiner—Howard Owens
(74) Attorney, Agent, or Firm—King & Spalding; Sherry M. Knowles, Esq.

(57) ABSTRACT

A method for the treatment of a host, and in particular, a human, infected with hepatitis B virus (HBV) is provided that includes administering an effective amount of a nucleotide prodrug of β- L-2', 3'-dideoxyadenosine, wherein the prodrug component of the nucleotide provides controlled delivery of the active species.

16 Claims, 2 Drawing Sheets

U.S. PATENT DOCUMENTS

| | | |
|---|---|---|
| 5,204,466 | 4/1993 | Liotta et al. . |
| 5,210,085 | 5/1993 | Liotta et al. . |
| 5,223,263 | 6/1993 | Hostetler et al. . |
| 5,234,913 | 8/1993 | Furman, Jr. et al. . |
| 5,248,776 | 9/1993 | Chu et al. . |
| 5,256,641 | 10/1993 | Yatvin et al. . |
| 5,270,315 | 12/1993 | Belleau et al. . |
| 5,276,151 | 1/1994 | Liotta . |
| 5,411,947 | 5/1995 | Hostetler et al. . |
| 5,444,063 | 8/1995 | Schinazi . |
| 5,463,092 | 10/1995 | Hostetler et al. . |
| 5,466,806 | 11/1995 | Belleau et al. . |
| 5,486,520 | 1/1996 | Belleau et al. . |
| 5,532,246 | 7/1996 | Belleau et al. . |
| 5,539,116 | 7/1996 | Liotta et al. . |
| 5,543,389 | 8/1996 | Yatvin et al. . |
| 5,543,390 | 8/1996 | Yatvin et al. . |
| 5,543,391 | 8/1996 | Yatvin et al. . |
| 5,554,728 | 9/1996 | Basava et al. . |
| 5,587,480 | 12/1996 | Belleau et al. . |
| 5,770,713 | 6/1998 | Imbach ................................ 536/22.1 |
| 5,770,725 | 6/1998 | Gosselin et al. ..................... 536/26.8 |
| 5,849,905 | 12/1998 | Gosselin et al. ................... 536/25.33 |

OTHER PUBLICATIONS

Beasley, et al., "Hepatocellular Carcinoma and Hepatitis B Virus," *The Lancet*, 1129–1133 (1981).

Belleau, B., et al., "Design and Activity of a Novel Class of Nucleoside Analogs . . . ," Intl. Conf. on AIDS, Montreal, Quebec, Canada, Jun. 4–9, 1989.

Boutelje, et al., *Chemical Abstracts* 108:128048 (1987).

Chang, C–N., et al., "Biochemical Phaarmacology of (+) and (–)–2',3'–Dideoxy–3'Thioacytidine as Anti–Hepatitis B Virus Agents," *J. Biol. Chem.* 267(31):22414–22420 (1992).

Chang, Chien–Neng, et al., "Deoxycytidine Deaminase–resistant Steroisomer is the Active Form of (+)–2'–3'–Thiacytidine in the Inhibition of Hepatitis B Virus Replication," *J. Bio. Chem.*, 267(20):13938–13942 (1992).

Chang, Chungming, et al., "Production of Hepatits B Virus in vitro by Transient Expression . . . ," *The EMBO J.* 6(3):675–680 (1987).

Chu, et al., "Structure–Activity Relationships of Pyrimide Nucleosides as Antiviral Agents for Human Immunodeficiency Virus Type 1 in Peripheral Blood Mononuclear Cells," *J. Med. Chem.*, 32:612 (1989)*.

Chu, et al., "Enantiomeric Synthesis of (+)–BCH–189[(=)–(2S,5R)–1–(Hydroxymethyl)–1,3–oxathiolane–5–yl]cytosine from D–Mannose and Its Anti–HIV Activity," *J. Org. Chem.*, 56:6503–6305 (1991).

Chu, C.K., et al., "An Efficient Total Synthesis of 3'–Azido–3'–Deoxythiymidine (AZT) and 3'–Azido–2', 3'–Dideoxyuridine (AZDDU, CS–87) from D–Mannitol," *Tetrahedron Lett.*, 29(42):5349–5352 (1988)*.

Chu, et al., "Comparative Activity of 2',3'–Saturated and Unsaturated Pyrimidine and Purine Nucleosides . . . ," *Biochem. Pharm.* 37(19):3543–3548 (1988)*.

Chu, et al., "Synthesis and Biological Evaluation of D–(2S) and L–(2R)–1,3–Oxathiolanyl– and D–(2R)– and L–(2S)–1, 3–Dioxolanyl–Nucleosides as Anti–HIV and Anti–HBV Agents," *Antiviral Research*, 30(S1):192 (Apr. 1993).

Chu, et al., "Synthesis and Anti–HIV and Anti–HBV Activity of Enantiomerically Pure Oxathiolane Nucleosides," *Antiviral Research*, 17(S1):2 (Mar. 1992).

Chu, et al., "Asymmetric Synthesis of Enantiomerically Pure (–)–(1'R,4'R)–Dioxolane–thymine and Its Anti–HIV Activity," *Tetrahedron Letters*, 32(31):3791–3794 (1991).

Coates, J., et al., "The Separated Enaniomers of 2'–deoxy–3'–thiacytidine (BCH–189) Both Inhibit Human Immunodeficiency Virus Replication In Vitro," *Antimicrob. Agents Chemother.* 36(1):202–205 (1992).

Cretton, E., et al., "Catabolism of 3'–Azido–3'–Deoxythymidine in Heptaocytes and Liver Microsomes, with Evidence of Formation of 3'–Amino–3'–Deoxythymidine a Highly Toxic Catabolite for Human Bone Marrow Cells," *Molecuilar Pharmacology*, 39:258–266 (1991)*.

Cretton, E., et al., "Pharmokinetics of 3'– Azido–3'–Dexoythymidine and its Catabolites and Interactions with Probenicid in Rhesus Monkeys," *Antimicrobial Agents and Chemotherapy*, 35(5):801–807 (1991)*.

Di Bisceglie, Adrian M., Rustgi, Vinod K. et al., "Hepatocellular Carcinoma," NIH Conference, *Annals of Internal Medicine*, 108:390–401 (1988).

Doong, Shin–Lian, et al., "Inhibition of the Replication of Hepatitis B virus in vitro by 2',3'–Dideoxy–3'–Thiacytidine and Related Analogues," *Natl. Acad. Sci. USA*, 88:8495–8499 (1991).

Furman, et al., "The Anti–Hepatitis B Virus Activities, Cytotoxicities, and Anabolic Profiles of the (–) and (+) Enantiomers of cis–5–Fluoro–1–[2–(Hydromethyl)–1, 3–Oxathiolane–5–yl) Cytosine," *Antim. Agents and Chemo.*, 36(12):2686–2692 (1992)*.

Ganem, "Animal Models of Hepatitis B Virus," *Experimental Models in Antimicrobial Chemotherapy*, 2:259–272 (1986)*.

Ganem, Don et al., "The Molecular Biology of the Hepatitis B Viruses," *Ann. Rev. Biochem.*, 56:651–693 (1987).

Gosselin, G., "Enantiomeric 2',3'–Deoxycytidine Derivatives are Potent Human Immunodeficiency Virus Inhibitors in Cell Cultures," *C.R. Acad. Sci. Paris Sci. Vie.* 317: 85–89 (1994).

Hamamoto, et al., *Antimicrob. Agents. Chemother.*, 31:907 (1987)*.

Hoong, et al., "Enzyme–Mediated Enantioselective Preparation of Pure Enantiomers of the Antiviral Agent 2'3'–Dideoxy–5–Fluoro–3'–Thiacytidine (FTC) and Related Compounds," *J. of Org. Chem.*, 57:5563–5565 (1992).

Jeong, L., et al., "Asymmetric Synthesis and Biological Evaluation of β–L–(2R,5S)– and a–L–(2R–5R)–1,3–Oxathiolane–Pyrimidine and –Purine Nucleosides and Potential Anti–HIV Agents," *J. Med. Chem.*, 36(2):181–195 (1993)*.

Jeong, et al., "An Efficient Synthesis of Enantiomerically Pure (+)–(2S,5R)–1–[2–(Hydroxymethyl)–1,3–oxathiolan–5–y;]cytosine [(+)–BCH–189] from D–Galactose," *Tetrahedron Letters*, 33(5):595–598 (1992).

Jones and Bischofberger, "Minireview: nucleotide prodrugs," *Antiviral Research*, 27:1–17 (1995).

Jurovcik and Holy, "Metabolism of pyrimidine L–nucleosides," *Nucleic Acid Research*, 3(8):2143–2154 (1976).

Kassianides, Chris, et al., "Inhibition of Duck Hepatitis B Virus Replication by 2',3'–Dideoxycytidine," *Gastroenterology*, 97(5):1275–1280 (1989).

Norin, *Chemical Abstracts*, 108:146380 (1987).

Ohno, et al., *Chemical Abstracts*, 112:194612 (1989).

Okabe, M., et al., "Synthesis of the Dideoxynucleosides ddC and CNT . . . ," *J. Org. Chem.*, 53(20):4780–4786 (1988)*.

Pai, S.B., et al., "Inhibition of Hepatitis B Virus by a Novel L–Nucleoside, 2'–Fluoro–5–Methyl–β–L–Arabinofuranosyl Uracil," *Antimicrobial Agents and Chemotherapy*, 40(2):380–386 (1996).

Richman, D. D., et al., "The Toxicity of Azidothymidine (AZT) in the Treatment of Patients with AIDS . . . ," *N. Eng. J. Med.*, 317(4):192–197 (1987*).

Ryan, K.J. et al., "9–β–L–Ribofuranosyladenine (L–Adenosine"), *Synthetic Procedures in Nucleic Acid Chemistry*, vol. 1, pp. 163–167, Interscience Publishers, New York, NY (1968).

Satsumabayashi, S. et al., "The Synthesis of 1,3–Oxathiolane–5–one Derivatives," *Bull. Chem. Soc. Japan*, 45:913–915 (1972)*.

Schinazi, et al., "Pure Nucleotide Enantiomers of β–2',3'–Dideoxycytidine Analogs are Selective Inhibitors of Hepatitis B Virus In Vitro," *Antimicrobial Agents and Chemotherapy*, 38(9):2172–2174 (1994)*.

Schinazi, R.F., et al., "Selective Inhibition of Human Immunodeficiency Viruses by Racemates and Enantiomers of cis–5–Fluoro–1–[2–(Hydroxymethyl)–1, 3–Oxathiolan–5–yl) Cytosine," *Antim. Agents and Chemo.*, 36(11):2423–2431 (1992)*.

Schinazi, R.F., et al., "Rapid Communications: Substrate Specificity of *Escherichia coli*.Thymidine Phosphorylase for Pyrimidine Nucleoside with an Anti–Human Immunodeficiency Virus Activity," *Bioch. Pharm.*, 44(2):199–204 (1992)*.

Schinazi, R.F., et al., "Activities of the Four Optical Isomers of 2',3'–Dideoxy–3'–Thiacytidine . . . ," *Antimic. Agents & Chemo.*, 36(3):672–676 (1992)*.

Schinazi, R.F., et al., "Insights into HIV Chemotherapy," *AIDS Research and Human Retroviruses* 8(6):963–989 (1992)*.

Schinazi, R.F., et al., "Pharmacokinetics and Metabolism of Racemic 2',3'–Dideoxy–5 . . . ," *Antimicrobial Agents and Chemotherapy* 36(11):2432–2438 (1992)*.

Schinazi, et al., *Antimicrob. Agents Chemother.*, 33:115 (1989).

Sells, Mary Ann, et al, "Production of Hepatitis B Virus Particles in Hep G2 Cells . . . ," *Proc. Natl. Acad. Sci. USA*, 84:1005–1009 (1987).

Soudeyns, H., et al., "Anti–Human Immunodeficiency Virus Type 1 Activity and In Vitro Toxicity of 2'–Deoxy–3'–Thiacytidine . . . ," *Antimicrobial Agents and Chemotherapy*, 35(7):1386–1390 (1991).

St. Clair, et al. *Antimicrob. Agents Chemother.*, 31:1972 (1987).

Sterzycki, R.Z., et al., "Synthesis and Anti–HIV Activity of Several 2'–Fluoro–Containing Pyrimidine Nucleosides," *J. Med. Chem.*, 33(8):2150–2157 (1990)*.

Storer, R., et al., "The Resolution and Absolute Stereochemistry of the Enantiomeris of cis–1–[2–(Hydromethyl)–1, 3–Oxathiolan–5–yl)cytosine (BCH–189): Equipotent Anti––HIV Agents," *Nucleosides & Nucleotides*, 12(2):225–236 (1993).

Su, Tsann–Long, et al., Nucleosides. 136. Synthesis and Antiviral Effects of Several 1–(2–Deoxy–2–Fluoro–β–D–Arabinofuranosyl)–5–Alkyluracils. Some Structure–Activity Relationships, *J. Med. Chem.*, 29(1):151–154 (1986).

Sureau, C., et al., "Production of Hepatitis B Virus by a Differentiated Human Hepatoma Cell Line after Transfection with Cloned Circular HBV DNA," *Cell*, 47:37–47 (1986).

Tsurimoto, Toshiki et al., "Stable Expression and Replication of Hepatitis B Virus Genome . . . ," *Proc. Natl. Acad. Sci. USA*, 84:444–448 (1987).

Volk, Wesley A., editor, "Hepatitis," *Essentials of Medical Microbiology*, J.B. Lippincott Company, (Philadelphia/Toronto), 2nd Ed., pp. 609–618 (1982).

Vorbrüggen, et al, "Nucleoside Synthesis with Trimethylsilyl Triflate and Perchlorate as Catalysts," *Chem. Ber.*, 114:1234–1255 (1981)*.

Watanabe, et al., *J. Med. Chem.*, 33:2145 (1990).

Wilson, L.J., et al., "The Synthesis and Anti–HIV Activity of Pyrimidine Dioxolanyl Nucleosides," *Bioorganic & Medicinal Chemistry Letters*, 3(2):169–174 (1993).

Wilson, L.J., et al., "A General Method for Controlling Glycosylation Stereochemistry in the Synthesis . . . ," *Tetrahedron Lett.*, 31(13):1815–1818 (1990)*.

Yokota et al., "Comparative Activities of Several Nucleoside Analogs Against Duck . . . ," *Antimicrobial Agents and Chemotherapy*, 34(7):1326–1330 (1990).

Zhu, Zhou, et al., "Cellular Metabolism of 3'–Azido–2', 3'–Dideoxyuridine with Formation of 5'–O–Diphophoshexase . . . " *Molecular Pharmacology*, 38:929–938 (1990)*.

NUCLEOSIDES WITH ANTI-HEPATITIS B VIRUS ACTIVITY

CROSS REFERENCE TO RELATED APPLICATION

This application is a continuation of U.S. Ser. No. 08/485,716, filed on Jun. 7, 1995, which is a continuation-in-part of U.S. patent application Ser. No. 08/320,461, filed Oct. 7, 1994, now abandoned which is incorporated herein by reference in its entirety.

BACKGROUND OF THE INVENTION

This invention is in the area of methods for the treatment of hepatitis B virus (also referred to as "HBV") that includes administering an effective amount of one or more of the active compounds disclosed herein, or a pharmaceutically acceptable derivative or prodrug of one of these compounds.

HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer. In western industrialized countries, high risk groups for HBV infection include those in contact with HBV carriers or their blood samples. The epidemiology of HBV is in fact very similar to that of acquired immunodeficiency syndrome, which accounts for why HBV infection is common among patients with AIDS or HIV-associated infections. However, HBV is more contagious than HIV.

Daily treatments with α-interferon, a genetically engineered protein, has shown promise. A human serum-derived vaccine has also been developed to immunize patients against HBV. Vaccines have been produced through genetic engineering. While the vaccine has been found effective, production of the vaccine is troublesome because the supply of human serum from chronic carriers is limited, and the purification procedure is long and expensive. Further, each batch of vaccine prepared from different serum must be tested in chimpanzees to ensure safety. In addition, the vaccine does not help the patients already infected with the virus.

European Patent Application No. 92304530.6 discloses that a group of 1,2-oxathiolane nucleosides are useful in the treatment of hepatitis B infections. It has been reported that the 2-hydroxymethyl-5-(cytosin-1-yl)-1,3-oxathiolane has anti-hepatitis B activity. Doong, et al., *Proc. of Natl. Acad. Sci USA*, 88, 8495–8499 (1991); Chang, et al., *J. of Biological Chem.*, Vol 267(20), 13938–13942. The anti-hepatitis B activity of the (−) and (+)-enantiomers of 2-hydroxymethyl-5-(5-fluorocytosin-1-yl)-1,3-oxathiolane has been published by Furman, et al., in *Antimicrobial Agents and Chemotherapy*, Dec. 1992, pages 2686–2692.

PCTAUS92/03144 (International Publication No. WO 92/18517) filed by Yale University discloses a number of β-L-nucleosides for the treatment of both HBV and HIV. Other drugs explored for the treatment of HBV include adenosine arabinoside, thymosin, acyclovir, phosphonoformate, zidovudine, (+)-cyanidanol, quinacrine, and 2'-fluoroarabinosyl-5-iodouracil. An essential step in the mode of action of purine and pyrimidine nucleosides against viral diseases, and in particular, HBV and V, is their metabolic activation by cellular and viral kinases, to yield the mono-, di-, and triphosphate derivatives. The biologically active species of many nucleosides is the triphospahte form, which inhibits DNA polymerase or reverse transcriptase, or causes chain termination. The nucleoside derivatives that have been developed for the treatment of HBV and HIV to date have been presented for administration to the host in unphosphorylated form, notwithstanding the fact that the nucleoside must be phosphorylated in the cell prior to exhibiting its antiviral effect, because the triphosphate form has typically either been dephosphorylated prior to reaching the cell or is poorly absorbed by the cell. Nucleotides in general cross cell membranes very inefficiently and are generally not very not very potent in vitro. Attempts at modifying nucleotides to increase the absorption and potency of nucleotides have been described by R. Jones and N. Bischofberger, *Antiviral Research*, 27 (1995) 1–17, the contents of which are incorporated herein by reference.

In light of the fact that hepatitis B virus has reached epidemic levels worldwide, and has severe and often tragic effects on the infected patient, there remains a strong need to provide new effective pharmaceutical agents to treat humans infected with the virus that have low toxicity to the host.

Therefore, it is another object of the present invention to provide a method and composition for the treatment of human patients or other hosts infected with HBV.

SUMMARY OF THE INVENTION

A method for the treatment of a host, and in particular, a human, infected with HBV is provided that includes administering an HBV-treatment amount of a nucleoside of the formula:

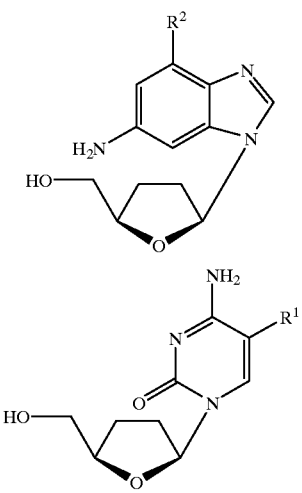

-continued

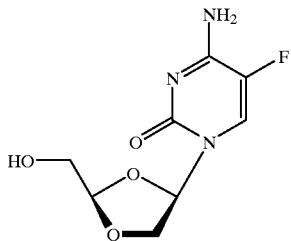

wherein:

R¹ is hydrogen, fluoro, bromo, chloro, iodo, methyl or ethyl; and R² is OH, Cl, NH₂, or H; or a pharmaceutically acceptable salt of the compound, optionally in a pharmaceutically acceptable carrier or diluent.

In an alternative embodiment, the β-L-enantiomer of a compound of the formula:

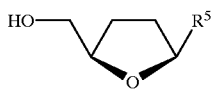

wherein R⁵ is adenine, xanthine, hypoxanthine, or other purine, including an alkylated or halogenated purine is administered to a host in an HBV-treatment amount as described more fully herein.

In another alternative embodiment, the nucleoside is of the formula:

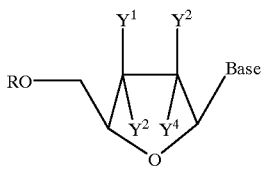

wherein B is a purine or pyrimidine base;

Y¹, Y², Y³, and Y⁴ are independently H, OH, N₃, NR¹R², NO₂, NOR³, —O-alkyl, —O-aryl, halo (including F, Cl, Br, or I), —CN, —C(O)NH₂, SH, —S-alkyl, or —S-aryl, and wherein typically three of Y¹, Y², Y³, and Y⁴ are either H or OH. The —OH substituent, when present, is typically a Y¹ or Y³ group. As illustrated in the structure, y² and Y⁴ are in the arabino (exytliro) configuration, and Y¹ and Y³ are in the threo (ribose) configuration. R is H, monophosphate, diphosphate, triphosphate, alkyl, acyl or a phosphate derivative, as described in more detail below. R¹, R², and R³ are independently alkyl (and in particular lower alkyl), aryl, aralkyl, alkaryl, acyl, or hydrogen.

In a preferred embodiment, the nucleoside is provided as the indicated enantiomer and substantially in the absence of its corresponding enantiomer (i.e., in enantiomerically enriched form).

In another embodiment, the invention includes a method for the treatment of humans infected with HBV that includes administering an HBV treatment amount of a prodrug of the specifically disclosed nucleosides. A prodrug, as used herein, refers to a pharmaceutically acceptable derivative of the specifically disclosed nucleoside, that is converted into the nucleoside on administration in vivo, or that has activity in itself. Nonlimiting examples are the 5' and N⁴-pyrimidine or N⁶-purine acylated or alkylated derivatives of the active compound.

In a preferred embodiment of the invention, the nucleoside is provided as the monophosphate, diphosphate or triphosphate in a formulation that protects the compound from dephosphorylation. Formulations include liposomes, lipospheres, microspheres or nanospheres (of which the latter three can be targeted to infected cells). In an alternative preferred embodiment, the nucleoside is provided as a monophosphate, diphosphate or triphosphate derivative (i.e., a nucleotide prodrug), for example an ester, that stabilizes the phosphate in vivo.

The disclosed nucleosides, or their pharmaceutically acceptable prodrugs or salts or pharmaceutically acceptable formulations containing these compounds are useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In one embodiment of the invention, one or more of the active compounds is administered in alternation or combination with one or more other anti-HBV agents, to provide effective anti-HBV treatment. Examples of anti-HBV agents that can be used in alternation or combination therapy include but are not limited to the (−)-enantiomer or racemic mixture of 2-hydroxymethyl-5-(5-fluorocytosin-1 -yl)-1,3-oxathiolane ("FTC", see WO 92/14743), its physiologically acceptable derivative, or physiologically acceptable salt; the (−)-enantiomer or racemic mixture of 2-hydroxymethyl-5-(cytosin-1-yl)-1,3-oxathiolane, its physiologically acceptable derivative, or physiologically acceptable salt; an enantiomer or racemic mixture of 2'-fluoro-5-iodo-arabinosyluracil (FIAU); an enantiomer or racemic mixture of 2'-fluoro-5-ethyl-arabinosyluracil (FEAU); carbovir, or interferon.

Any method of alternation can be used that provides treatment to the patient. Nonlimiting examples of alternation patterns include 1–6 weeks of administration of an effective amount of one agent followed by 1–6 weeks of administration of an effective amount of a second anti-HBV agent. The alternation schedule can include periods of no treatment. Combination therapy generally includes the simultaneous administration of an effective ratio of dosages of two or more anti-HBV agents.

In light of the fact that HBV is often found in patients who are also anti-HIV antibody or HIV-antigen positive or who have been exposed to HIV, the active anti-HBV compounds disclosed herein or their derivatives or prodrugs can be administered in the appropriate circumstance in combination or alternation with anti-HIV medications, including but not limited to 3'-azido-3'-deoxythymidine (AZT), 2', 3'-dideoxyinosine (DDI), 2', 3'-dideoxycytidine (DDC), 2', 3'-dideoxy-2', 3'-didehydrothymidine (D4T), 2-hydroxymethyl-5-(5-fluorocytosin-1-yl)-1,3-oxathiolane (FTC), or 2-hydroxymethyl-5-(cytosin-1-yl)-1,3-oxathiolane (BCH-189), in racemic or enantiomeric form. Non-nucleoside RT-inhibitors such as the Tibo class of compounds, nevirapine, or pyrimidinone can also be administered in combination with the claimed compounds.

The active anti-HBV agents can also be administered in combination with antibiotics, other antiviral compounds, antifunigal agents, or other pharmaceutical agents administered for the treatment of secondary infections.

DETAILED DESCRIPTION OF THE INVENTION

Figure 1:
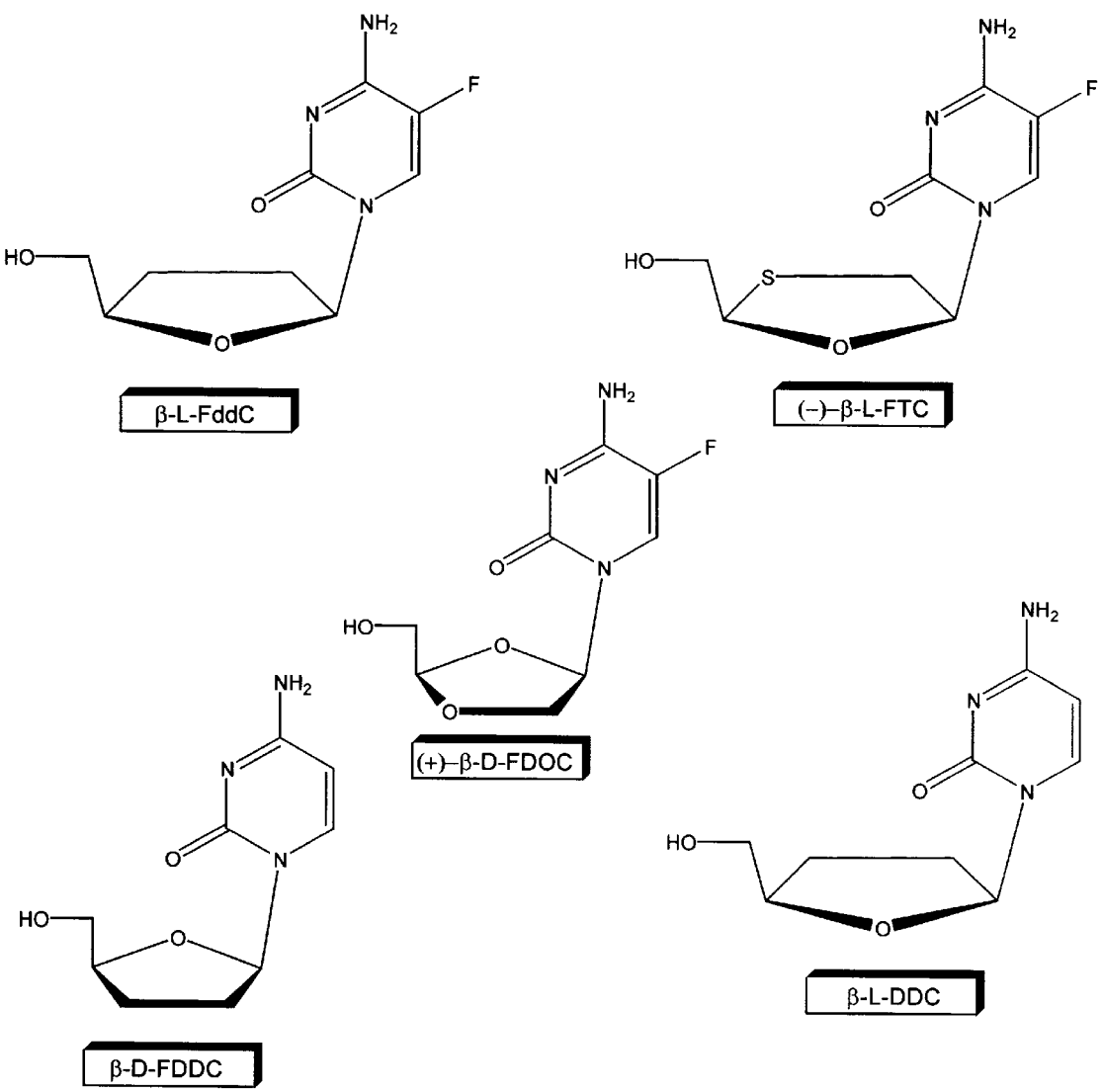
FIG. 1 is an illustration of the chemical structures of β-L-2', 3'-dideoxycytidine (β-L-FddC), β-D-2', 3'-dideoxycytidine (β-D-ddC), β-L-2', 3'-dideoxy-5-fluorocytidine (β-L-ddC), (−)-β-L-2-hydroxymethyl-5-(5-fluorocytosin-1-yl)-1,3-oxathiolane ((−)-β-L-FTC), (+)-β-D-2-hydroxymethyl-5-(5-fluorocytosin-1-yl)-1,3-dioxolane ((+)-β-D-FDOC), and β-L-2-amino-6-($R^4$)-9-[(4hydroxymethyl)-tetrahydrofuran-1-yl]purine.

As used herein, the term "enantiomerically pure" refers to a nucleoside composition that includes at least approximately 95%, and preferably approximately 97%, 98%, 99%, or 100% of a single enantiomer of that nucleoside.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991. The term lower alkyl, as used herein, and unless otherwise specified, refers to a $C_1$ to $C_4$ ethyl, propyl, butyl, pentyl, hexyl, isopropyl, isobutyl, sec-butyl, or t-butyl group.

As used herein, the term acyl specifically includes but is not limited to acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic.

The term aryl, as used herein, and unless otherwise specified, refers to phenyl, biphenyl, or naphthyl, and preferably pbenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, N6-thioalkyl purine, $N^2$-alkylpurines, $N^2$-alkyl-6-thiopurines, thymine, cytosine, 6azapyrimidine, 2- and/or 4-mercaptopyrmidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkylpurine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, pyrazolopyrimidi-nyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methylsulfonyl, and p-toluylsulfonyl.

As used herein, the term natural amino acid includes but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The invention as disclosed herein is a method and composition for the treatment of HBV infection and other viruses replicating in a like manner, in humans or other host animals, that includes administering an effective amount of one or more of the above-identified compounds, or a physiologically acceptable derivative, or a physiologically acceptable salt thereof, optionally in a pharmaceutically acceptable carrier. The compounds of this invention either possess anti-HBV activity, or are metabolized to a compound or compounds that exhibit anti-HBV activity.

I. Structure and Preparation of Active Nucleosides

Stereochemishy

The compounds used in the methods disclosed herein are enantiomers of 2', 3'-dideoxycytidine, 2', 3'-dideoxy-5-(halo or methyl)cytidine, 2-hydroxymethyl-5-(5-fluorocytosin-1-yl)-1,3-dioxolane, or 2-amino-6-(OH, Cl, $NH_2$, or H)-9-[(4-hydroxymethyl)-tetrahydrofuran-1-yl]purine.

Since the 1' and 4' carbons of the sugar or dioxolanyl moiety (referred to below generically as the sugar moiety) of the nucleosides are chiral, their nonhydrogen substituents ($CH_2OR$ and the pyrimidine or purine base, respectively) can be either cis (on the same side) or trans (on opposite sides) with respect to the sugar ring system. The four optical isomers therefore are represented by the following configurations (when orienting the sugar moiety in a horizontal plane such that the "primary" oxygen (that between the C1' and C4'-atoms; see FIG. 2) is in back): cis (with both groups "up", which corresponds to the configuration of naturally occurring nucleosides), cis (with both groups "down", which is a nonnaturally occurring configuration), trans (with the C2 substituent "up" and the C5 substituent "down"), and trans (with the C2 substituent "down" and the C5 substituent "up"). As indicated schematically in FIG. 1, the "D-nucleosides" are cis nucleosides in a natural configuration and the "L-nucleosides" are cis nucleosides in the nonnaturally occurring configuration.

The nucleosides useful in the disclosed method to treat HBV infection are β-L-enantiomers, with the exception of FDOC, which is used in its β-D-enantiomeric form, because it has been discovered that the β-D-enantiomer of FDOC is surprisingly less toxic than the β-L-enantiomer of FDOC.

Prodrug Formulations

The nucleosides disclosed herein can be administered as any derivative that upon administration to the recipient, is capable of providing directly or indirectly, the parent active compound, or that exhibits activity in itself. In one embodiment, the hydrogen of the 5'-OH group is replaced by a $C_1$–$C_{20}$ alkyl; acyl in which the non-carbonyl moiety of the ester group is selected from straight, branched, or cyclic $C_1$–$C_{20}$ alkyl, phenyl, or benzyl; a naturally occurring or nonnaturally occurring amino acid; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy; a dicarboxylic acid such as succinic acid; sulfonate esters such as alkyl or aralkyl sulphonyl including methanesulfonyl; or a mono, di or triphosphate ester.

One or both hydrogens of the amino groups on the purine or pyrimidine base can be replaced by a $C_1$-$C_{20}$ alkyl; acyl in which the noncarbonyl moiety of the ester group is selected from straight, branched, or cyclic $C_1$-$C_{20}$ alkyl, phenyl, or benzyl; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy.

The active nucleoside can also be provided as a 5'-ether lipid, as disclosed in the following references, which are incorporated by reference herein: Kucera, L. S., N. Iyer, E. Leake, A. Raben, Modest E. J., D. L. W., and C. Piantadosi. 1990. Novel membrane-interactive ether lipid analogs that inhibit infectious HIV-1 production and induce defective virus formation. AIDS Res Hum Retroviruses. 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. Synthesis and evaluation of novel ether lipid nucleoside conjugates for anti-HIV activity. J Med Chem. 34:1408.1414; Hostetler, K. Y., D. D. Richman, D. A. Carson, L. M. Stuhmiller, G. M. T. van Wijk, and H. van den Bosch. 1992. Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine. Antimicrob Agens Chemother. 36:2025.2029; Hostetler, K. Y., L. M. Stuhmiller, H. B. Lenting, H. van den Bosch, and D. D. Richman, 1990. Synthesis and antiretroviral activity of phospholipid analogs of azidothymidine and other antiviral nucleosides. J. Biol Chem. 265:6112.7.

Nucleotide Prodrugs

Any of the nucleosides described herein can be administered as a nucleotide prodrug to increase the activity, bioavalability, stability or otherwise alter the properties of the nucleoside. A number of nucleotide prodrug ligands are known. In general, alkylation, acylation or other lipophilic modification of the mono, di or triphosphoate of the nucleoside will increase the stability of the nucleotide. Examples of substituent groups that can replace one or more hydrogens on the the phosphate moiety are alkyl, aryl, steroids, carbohydrates, including sugars, 1,2-diacylglycerol and alcohols. Many are described in R Jones and N. Bischofberger, Antiviral Research, 27 (1995) 1–17. Any of these can be used in combination with the disclosed nucleosides to achieve a desired effect. Nonlimiting examples of nucleotide prodrugs are described in the following references.

Ho, D. H. W. (1973) Distribution of Kinase and deaminase of 1β-D-arabinofiuranosylcytosine in tissues of man and muse. Cancer Res. 33, 2816–2820; Holy, A. (1993) Isopolar phosphorous-modified nucleotide analogues. In: De Clercq (Ed.), Advances in Antiviral Drug Design, Vol. 1, JAI Press, pp. 179–23 1; Hong, C. I., Nechaev, A., and West, C. R. (1979a) Synthesis and antitumor activity of 1β-D-arabinofuranosylcytosine conjugates of cortisol and cortisone. Biochem. Biophys. Rs. Commun. 88, 1223–1229; Hong, C. I., Nechaev, A., Kirisits, A. J. Buchheit, D. J. and West, C. R. (1980) Nucleoside conjugates as potential antitumor agents. 3. Synthesis and antitumor activity of 1-(β-D-arabinofiuranosyl)cytosine conjugates of corticosteriods and selected lipophilic alcohols. J. Med. Chem. 28, 171–177; Hostetler, K. Y., Stuhmiller, L. M., Lenting, H. B. M. van den Bosch, H. and Richman, D. D. (1990) Synthesis and antiretrioviral activity of phospholipid analogs of azidothymidine and other antiviral nucleosides. J Biol. Chem. 265, 6112–6117; Hostetler, K. Y., Carson, D. A. and Richman, D. D. (1991); Phosphatidylazidothymidine: mechanism of antiretroviral action in CEM cells. J. Biol. Chem. 266, 11714–11717; Hostetler, K. Y., Korba, B. Sridhar, C., Gardener, M. (1994a) Antiviral activity of phosphatidyl-dideoxycytidine in hepatitis B-infected cells and enhanced hepatic uptake in mice. Antiviral Res. 24, 59–67; Hostetler, K. Y., Richman, D. D., Sridhar, C. N. Felgner, P. L, Felgner, J., Ricci, J., Gardener, M. F. Selleseth, D. W. and Ellis, M. N. (1994b) Phosphatidylazidothymidine and phosphatidyl-ddC: Assessment of uptake in mouse lymphoid tissues and antiviral activities in human immunodeficiency virus-infected cells and in rauscher leukemia virus-infected mice. Antimicrobial Agents Chemother. 38, 2792–2797; Hunston, R. N., Jones, A. A. McGuigan, C., Walker, R. T., Balzarini, J., and De Clercq, E. (1984) Synthesis and biological properties of some cyclic phosphotriesters derived from 2'-deoxy-5-fluorouridine. J. Med. Chem. 27,440–444; Ji, Y. H., Moog, C., Schmitt, G., Bischoff, P. and Luu, B. (1990); Monophosphoric acid diesters of 7β-hydroxycholesterol and of pytimidine nucleosides as potential antitumor agents: synthesis and preliminary evaluation of antitumor activity. J. Med Chem. 33, 2264–2270; Jones, A. S., McGuigan, C., Walker, R. T., Baizarini, J. and DeClercq, E. (1984) Synthesis, properties, and biological activity of some nucleoside cyclic phosphoramidates. J Chem. Soc. Perkin Trans. 1, 1471–1474; Juodka, B. A. and Smrt, J. (1974) Synthesis of ditribonucleoside phosph(P→N) amino acid derivatives. Coll. Czech. Chem. Comm. 39,363–968; Kataoka, S., Imai, J., Yamaji, N., Kato, M., Saito, M., Kawada, T. and Imai, S. (1989) Alkylacted cAMP derivatives; selective synthesis and biological activities. Nucleic Acids Res. Sym. Ser., 21, 1–2; Kataoka, S., Uchida, R. and Yamaji, N. (1991) A convenient synthesis of adenosine 3', 5'cyclic phosphate (cAMP) benzyl and methyl triesters. Heterocycles 32, 1351–1356; Kinchington, D., Harvey, J. J., O'Connor, T. J., Jones, B. C. N. M., Devine, K. G., Taylor-Robinson, D., Jeffries, D. J. and McGuigan, C. (1992) Comparison of antiviral effects of zidovudine phosphoramidate and phosphorodiamidate derivatives against HIV and ULV in vitro. Antiviral Chem. Chemother. 3, 107–112; Kodama, K., Morozumi, M., Saitoh, K. I., Kuninaka, H., Yoshino, H. and Saneyoshi, M. (1989) Antitumor activity and pharmacology of 1-β-D-arabinofuranosylcytosine -5'-stearylphosphate; an orally active derivative of 1-β-D-arabinofuranosylcytosine. Jpn. J. Cancer Res. 80, 679–685; Korty, M. and Engels, J. (1979) The effects of adenosine- and guanosine 3', 5'phosphoric and acid benzyl esters on guinea-pig ventricular myocardium. Naunyn-Schmiedeberg's Arch. Pharmacol. 310, 103–111; Kumar, A., Goe, P. L., Jones, A. S. Walker, R. T. Balzarini, J. and De Clercq, E. (1990) Synthesis and biological evaluation of some cyclic phosphoramidate nucleoside derivatives. J. Med. Chem. 33, 2368–2375; LeBec, C., and Huynh-Dinh, T. (1991) Synthesis of lipophilic phosphate triester derivatives of 5-fluorouridine and arabinocytidine as anti-cancer prodrugs. Tetrahedron Lett. 32,6553–6556; Lichtenstein, J., Bamer, H. D. and Cohen, S. S. (1960) The metabolism of exogenously supplied nucleotides by Escherichia coli., J. Biol. Chem. 235, 457–465; Lucthy, J., Von Daeniken, A., Friederich, J. Manthey, B., Zweifel, J., Schlatter, C. and Benn, M. H. (1981) Synthesis and toxicological properties of three naturally occurring cyanoepithioalkanes. Mitt. Geg. Lebensmittelunters. *Hyg.* 72, 131–133 (*Chem. Abstr.* 95, 127093); McGuigan, C. Tollerfield, S. M. and Riley, P. A. (1989) Synthesis and biological evaluation of some phosphate triester derivatives of the anti-viral drug Ara. *Nucleic Acids Res.* 17, 6065–6075; McGuigan, C., Devine, K. G., O'Connor, T. J., Galpin, S. A., Jeffties, D. J. and Kinchington, D. (1990a) Synthesis and evaluation of some novel phosphoramidate derivatives of 3'-azido-3'deoxythymidine (AZT) as anti-HIV compounds. *Antiviral Chem. Chemother.* 1, 107–113; McGuigan, C., O'Connor, T. J., Nicholls, S. R. Nickson, C. and Kinchington, D. (1990b) Synthesis and anti-HIV activity of some novel substituted dialky phosphate derivatives of AZT and ddCyd. *Antiviral Chem. Chemother.* 1, 355–360; McGuigan, C., Nicholls, S. R., O'Connor, T. J., and Kinchington, D. (1990c) Synthesis of some novel dialkyl phosphate derivative of 3'-modified nucleosides as potential anti-AIDS drugs. *Antiviral Chem. Chemother.* 1, 25–33; McGuigan, C., Devine, K. G., O'Connor, T. J., and Kinchington, D.(1991) Synthesis and anti-HIV activity of some haloalky phosphoramidate derivatives of 3'-azido-3'deoxythylmidine (AZT); potent activity of the trichloroethyl methoxyalaninyl compound. *Antiviral Res.* 15, 255–263; McGuigan, C., Pathirana, R.N., Malimood, N., Devine, K. G. and Hay, A. J. (1992) Aryl phosphate derivatives of AZT retain activity against HIV1 in cell lines which are resistant to the action of AZT. Antiviral Res. 17, 311–321; McGuigan, C., Pathirana, R. N., Choi, S. M., Kinchington, D. and O'Connor, T. J. (1993a) Phosphoramidate derivatives of AZT as inhibitors of HIV; studies on the carboxyl terminus. *Antiviral Chem. Chemother.* 4,97–101; McGuigan, C., Pathirana, R. N., Balzarini, J. and De Clercq, E. (1993b) Intracellular delivery of bioactive AZT nucleotides by aryl phosphate derivatives of AZT. *J. Med. Chem.* 36, 1048–1052.

Alky hydrogen phosphonate derivatives of the anti-HIV agent AZT may be less toxic than the parent nucleoside analogue. *Antiviral Chem. Chemother.* 5, 271–277; Meyer, R. B., Jr., Shuman, D. A. and Robins, R. K. (1973) Synthesis of purine nucleoside 3', 5'-cyclic phosphoramidates. *Tetrahedron Lett.* 269–272; Nagyvary, J. Gohil, R. N., Kirchner, C. R. and Stevens, J. D. (1973) Studies on neutral esters of cyclic AMP, *Biochem. Biophys. Res. Commun.* 55, 1072–1077; Namane, A. Gouyette, C., Fillion, M. P., Fillion, G. and Huynh-Dinh, T. (1992) Improved brain delivery of AZT using a glycosyl phosphotriester prodrug. J. Med. Chem. 35, 3039–3044; Nargeot, J. Nerbonne, J. M. Engels, J. and Leser, H. A. (1983) Natl. Acad. Sci. U.S.A. 80, 2395–2399; Nelson, K. A., Bentrude, W. G., Stser, W. N. and Hutchinson, J. P. (1987) The question of chair-twist equilibria for the phosphate rings of nucleoside cyclic 3', 5'monophosphates. HNMR and x-ray crystallographic study of the diasteromers of thymidine phenyl cyclic 3', 5'-monophosphate. J. Am. Chem. Soc. 109,4058–4064; Nerbonne, J. M., Richard, S., Nargeot, J. and Lester, H. A. (1984) New photoactivatable cyclic nucleotides produce intracellular jumps in cyclic AMP and cyclic GMP concentrations. Nature 301, 74–76; Neumann, J. M., Herve, M., Debouzy, J. C., Guerra, F. I., Gouyette, C., Dupraz, B. and Huynh-Dinh, T. (1989) Synthesis and transmembrane transport studies by NMR of a glucosyl phospholipid of thymidine. J. Am. Chem. Soc. 111, 42704277; Ohno, R., Tatsumi, N., Hirano, M., Imai, K. Mizoguchi, H., Nakamura, T., Kosaka, M., Takatuski, K., Yamaya, T., Toyama, K., Yoshida, T., Masaoka, T., Hashimoto, S., Ohshima, T., Kimura, I., Yamada, K. and Kimura, J. (1991) Treatment of myelodysplastic syndromes with orally administered 1-β-D-rabinofuranosylcytosine -5'stearylphosphate. Oncology 48, 451–455.

Palomino, E., Kessle, D. and Horwitz, J. P. (1989) A dihydropyridine carrier system for sustained delivery of 2', 3'dideoxynucleosides to the brain. J. Med. Chem. 32, 622–625; Perkins, R. M., Barney, S., Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) Activity of BRL47923 and its oral prodrug, SB203657A against a rauscher murine leukemia virus infection in mice. Antiviral Res. 20 (Suppl. I). 84; Piantadosi, C., Marasco, C. J., Jr., Morris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) Synthesis and evaluation of novel ether lipid nucleoside conjugates for anti-HIV-1 activity. J. Med. Chem. 34, 1408–1414; Pompon, A., Lefebvre, I., Imbach, J.L., Kahn, S. and Farquhar, D. (1994) Decomposition pathways of the mono- and bis (pivaloyloxymethyl) esters of azidothymidine-5'-monophosphate in cell extract and in tissue culture medium; an application of the on-line ISRP-cleaning' HPLC technique. Antiviral Chem. Chemother. 5, 91–98; Postemark, T. (1974) Cyclic AMP and cyclic GMP. Annu. Rev. Pharmacol. 14, 23–33; Prisbe, E. J., Martin, J. C. M., McGee, D. P. C., Barker, M. F., Smee, D. F. Duke, A. E., Matthews, T. R. and Verheyden, J. P. J. (1986) Synthesis and antiherpes virus activity of phosphate an phosphonate derivatives of 9-[(1,3-dihydroxy-2-propoxy)methyl]guanine. J. Med. Chem. 29, 671–675; Pucch, F., Gosselin, G., Lefebvre, I., Pompon, A., Aubertin, A. M. Dirn, A. and Imbach, J. L. (1993) Intracellular delivery of nucleoside monophosphate tbrough a reductase-mediated activation process. Antiviral Res. 22, 155–174; Pugaeva, V. P., Klochkeva, S. I., Mashbits, F. D. and Eizengart, R. S. (1969). Toxicological assessment and health standard ratings for ethylene sulfide in the industrial atmosphere. Gig. Trf. Prof. Zabol. 13, 47–48 (Chem. Abstr. 72, 212); Robins, R. K. (1984) The potential of nucleotide analogs as inhibitors of retroviruses and tumors. Pharm. Res. 11 –18; Rosowsky, A., Kim. S. H., Ross and J. Wick, M. M. (1982) Lipophilic 5'-(alkylphosphate) esters of 1β-D-arabinofuranosylcytosing and its $N^4$-acyl and 2.2'-anhydro-3'0-acyl derivatives as potential prodrugs. J. Med. Chem. 25, 171–178; Ross, W. (1961) Increased sensitivity of the walker turnout towards aromatic nitrogen mustards carrying basic side chains following glucose pretreatment. Biochem. Phaim. 8,235–240; Ryu, e. K., Ross, R. J. Matsushita, T., MacCoss, M., Hong, C. I. and West, C. R. (1982). Phospholipid-nucleoside conjugates. 3. Synthesis and preliminary biological evaluation of 1-β-D-arabinofuranosylcytosine 5'diphosphate[−], 2-diacylglycerols. J. Med. Chem. 25, 1322–1329; Saffliill, R. and Hume, W. J. (1986) The degradation of 5-iododeoxyurindine and 5-bromoeoxyuridine by serum from different sources and its consequences for the use of these compounds for incorporation into DNA. Chem. Biol. Interact. 57, 347–355; Saneyoshi, M., Morozumi, M., Kodama, K., Machida, J., Kuninaka, A. and Yoshino, H. (1980) Synthetic nucleosides and nucleotides. XVI. Synthesis and biological evaluations of a series of 1-β-D-arabinofuranosylcytosine 5'-alky or arylphosphates. Chem. Pharm. Bull. 28, 2915–2923; Sastry, J. K., Nehete, P. N., Khan, S., Nowak, B. J., Plunkett, W., Arlinghaus, R. B. and Farquhar, D. (1992) Membrane-permeable dideoxyuridine 5'-monophosphate analogue inhibits human immunodeficiency virus infection. Mol. Pharimacol. 41, 441 445; Shaw, J. P., Jones, R. J. Arimilli, M. N., Louie, M. S., Lee, W. A. and Cundy, K. C. (1994) Oral bioavailability of PMEA from PMEA prodrugs in male Sprague-Dawley rats. 9th Annual AAPS Meeting. San Diego, Calif. (Abstract). Shuto, S., Ueda, S., Imamura, S., Fukukawa, K. Matsuda, A. and Ueda, T. (1987) A facile one-step synthesis of Sphosphatidyl-nucleosides by an enzymatic two-phase reaction. Tetrahedron Lett. 28, 199–202; Shuto, S., Itoh, H., Ueda, S., Imamura, S., Kukukawa, K., Tsujino, M., Matsuda, A. and Ueda, T. (1988) A facile enzymatic synthesis of 5'-(3-sn-phosphatidyl)nucleosides and their antileukemic activities. Chem. Pharm. Bull. 36,209–217. A preferred phosphate prodrug group is the S-acyl-2-thioethyl group, also referred to as "SATE".

Preparation of the Active Compounds

The nucleosides used in the disclosed method to treat HBV infections in a host organism can be prepared according to published methods. β-L-Nucleosides can be prepared from methods disclosed in, or standard modifications of methods disclosed in, for example, the following publications: Jeong, et al., J. of Med. Chem., X, 182–195, 1993; European Patent Application Publication No. 0 285 884; Génu-Dellac, C., G. Gosselin, A.-M. Aubertin, G. Obert, A. Kim, and J.-L. Imbach, 3-Substituted thymine α-L-nucleoside derivatives as potential antiviral agents; synthesis and biological evaluation, Antiviral Chem. Chemo. 2:83–92 (1991); Johansson, K. N. G., B. G. Lindborg, and R. Noreen, European Patent Application 352 248; Mansuri, M. M., V. Farina, J. E. Starrett, D. A. Benigni, V. Brankovan, and J. C. Martin, Preparation of the geometric isomers of DDC, DDA, D4C and D4T as potential anti-HIV agents, Bioorg. Med. Chem. Lett. 1:65–68 (1991); Fujimori, S., N. Iwanami, Y. Hashimoto, and K. Shudo, A convenient and stereoselective synthesis of 2'-deoxy-β-L-ribonucleosides, Nucleosides & Nucleotides 11:341–349 (1992); Genu-Dellac, C., G. Gosselin, A. -M. Aubertin, G. Obert, A. Kim, and J.-L. Imbach, 3-Substituted thymine α-L-nucleoside derivatives as potential antiviral agents; synthesis and biological evaluation, Antiviral Chem, Chemother 2:83–92 (1991); Holy, A, Synthesis of 2'-deoxy-L-uridine, Tetrahedron Lett. 2:189–192 (1992); Holy, A., Nucleic acid components and their analogs. CLIII. Preparation of 2'-deoxy-L-ribonucleosides of the pyrimidine series. Collect Czech Chem Commun. 37:4072–4087 (1992); Holy, A, 2'-deoxy-L-uridine: Total synthesis of a uracil 2'-deoxynucleoside from a sugar 2-arninooxazoline through a 2.2'-anhydronucleoside intermediate. In: Townsend L B, Tipson R S, ed. Nucleic Acid Chem. New York: Wiley, 1992: 347–353. vol 1) (1992); Okabe, M., R.-C. Sun, S. Tan, L. Todaro, and D. L. Coffen, Synthesis of the dideoxynucleosides ddC and CNT from glutamic acid, ribonolactone, and pyrimidine bases. J Org Chem. 53:47804786 (1988); Robins, M. J., T. A. Khva, and R. K. Robins. Purine nucleosides. XXIX. Synthesis of 21-deoxy-L-adenosine and 21-deoxy-L-guanosine and their alpha anomers. J Org Chem. 35:363–639 (1992); Génu-Dellac, C., Gosselin G., Aubertin A- M, Obert G., Kim A., and Imbach J-L, 3'-Substituted thyrnine α-L-nucleoside derivatives as potential antiviral agents; synthesis and biological evaluation. Antiviral Chem, Chemother. 2(2):83–92 (1991); Genu-Dellac, C., Gosselin G., Imbach J -L; Synthesis of new 2'-deoxy-3'-substituted-a-L-threo-pentofuranonucleosides of thymine as a potential antiviral agents. Tet Lett 32(l) :79–82 (1991); Génu-Dellac, C., Gosselin G., Imbach J-L. Preparation of new acylated derivatives of L-arabinofuranose and 2-deoxy-1-erythro-pentofuranose as precursors for the synthesis of 1-pentofuranosyl nucleosides. 216:240–255 (1991); and Genu-Dellac, C., Gosselin G., Puech F, et al. Systematic synthesis and antiviral evaluation of α-L-arabinofuranosyl and 2'-deoxy-α-L-erythro-pentofuranosyl nucleosides of the five naturally occurring nuclei acid bases. 10(b):1345–1376 (1991).

2', 3'-Dideoxycytidine (DDC) is a known compound. The D-enantiomer of DDC is currently being marketed by Hoffinan-LaRoche under the name Zalcitabine for use in the treatment of persons infected with HIV. See U.S. Pat. Nos. 4,879,277 and 4,900,828.

Enantiomerically pure β-D-dioxolane-nucleosides such as β-D-FDOC can be prepared as disclosed in detail in PCT/US91/09124. The process involves the initial preparation of (2R,4R)- and (2R,4S)-4-acetoxy-2-(protected-oxymethyl)-dioxolane from 1,6anhydromannose, a sugar that contains all of the necessary stereochemistry for the enantiomerically pure final product, including the correct diastereomeric configuration about the 1 position of the sugar (that becomes the 4'-position in the later formed nucleoside). The (2R,4R) and (2R,4S)-4-acetoxy-2-(protected-oxymethyl)-dioxolane is condensed with a desired heterocyclic base in the presence of $SnCl_4$, other Lewis acid, or trimethylsilyl triflate in an organic solvent such as dichloroethane, acetonitrile, or methylene chloride, to provide the stereochemically pure dioxolane-nucleoside.

Enzymatic methods for the separation of D and L enantiomers of cis-nucleosides are disclosed in, for example, Nucleosides and Nucleotides, 12(2), 225–236 (1993); European Patent Application Nos. 92304551.2 and 92304552.0 filed by Biochem Pharma, Inc.; and PCT Publication Nos. WO 91/11186, WO 92/14729, and WO 92/14743 filed by Emory University.

Separation of the acylated or alkylated racemic mixture of D and L enantiomers of cis-nucleosides can be accomplished by high performance liquid chromatography with chiral stationary phases, as disclosed in PCT Publication No. WO 92/14729.

Mono, di, and triphosphate derivative of the active nucleosides can be prepared as described according to published methods. The monophosphate can be prepared according to the procedure of Imai et al., J. Org. Chem., 34(6), 1547–1550 (June 1969). The diphosphate can be prepared according to the procedure of Davisson et al., J. Org. Chem., 52(9), 1794–1801 (1987). The triphosphate can be prepared according to the procedure of Hoard et al., J. Am. Chem. Soc., 87(8), 1785–1788 (1965).

General Procedures for the Preparation of Bis (S-acyl-2-thioethyl) Phosphoester of β-L-dideo ynucleosides [Bis (SATE) β-L ddx MP]

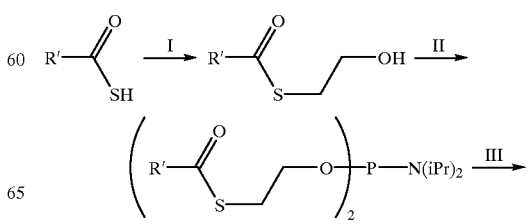

-continued

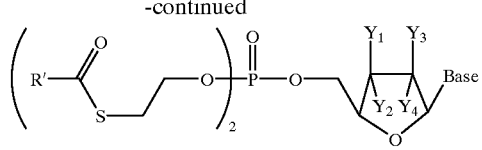

Bis (SATE) β-L-ddxMP $Y_1$, $Y_2$, l $Y_3$, $Y_4$=H, F, $N_3$, $NR_1R_2$, $NO_2$, NOR, O-alkyl, O-aryl . . .

R=$CH_3$, $(CH_3)_2$ CH, $(CH_3)_3$C, $C_6H_5$. . .

(i) $ICH_2CH_2OH$, $DBU/C_6H_5CH_3$; (ii) $Cl_2PN(iPr)2$, $NEt_3$/TBF; (iii) β-L-dideoxynucleoside, 1H—tetrazolen/THF, then $ClC_6H_4CO_3H/CH_2Cl_2$ 1H-Tetrazole (0.21g, 3.0 mmol) was added to a stirred solution of β-L-dideoxynucleoside (1.0 mmol) and the appropriate phosphoramidite C (1.2 mmol) in tetrahydrofuran (2mL) at room temperature. After 30 minutes, the reaction mixture was cooled to −40° C. and a solution of 3-chloroperoxybenzoic acid (0.23 g, 1.3 mmol) in dichloromethane (2.5 mL) was added; the mixture was then allowed to warm to room temperature over 1 h. Sodium sulfite (10% solution, 1.3 mL) was added to the mixture to destroy the excess 3-chloroperoxybenzoic acid, after which the organic layer was separated and the aqueous layer washed with dichloromethane (2×10 mL). The combined organic layers were washed with saturated aqueous sodium hydrogen carbonate (5 mL), then water (3×5 mL), dried over sodium sulfate, filtered and evaporated to dryness under reduced pressure. Column chromatography of the residue on silica gel afforded the title Bis(SATE) β-L-ddxmP.

EXAMPLE=β-L-2', 3'-Dideoxyadenosin-5'-yl bis (2-pivaloylthioethyl) phosphate [Bis (SATE) β-L-ddE]

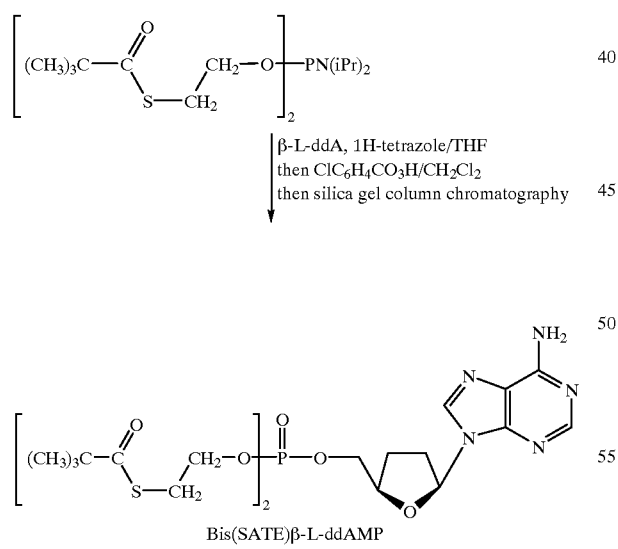

Following the above general procedure, pure Bis(SATE) β-L-ddAMP was obtained as a colorless oil in 72% yield after silica gel column chromatography [eluent: stepwise gradient of methanol (0–3%) in dichloromethane]; $^1$NMR (DMSO - $d_6$) δppm: 8.26 and 8.13 (2s, 2H each, H-2 and H-8), 7.20 (br s, 2H, $NH_2$), 6.24 (t, 1H, H-1'; J=6.0 Hz), 4.35–4.25 (m, 1H, H-4'), 4.25–4.00 (m, 2H, H-5', 5"), 3.96 (m, 4H, 2 $SCH_2CH_2O$), 3.04 (t, 4H, 2 $SCH_2CH_2O$; J=6.3 Hz), 2.5–2.4 (m, 2H, H-2', 2") 2.2–2.0 (m, 2H, H-3', 3"), 1.15 [s, 18H, 2 $(CH_3)_3C$]; $^{31}$P-NMR (DMSO-$d_6$) δppm=−0.76 (s); UV (EtOH), $\lambda_{max}$=259 nm (ϵ15400); mass spectum (performed in: glycerol, thioglycerol, 1:1, υ/υ), FAB>O 604 $(M+H)^+$, 136 $(BH_2)^+$.

General scheme for the sterospecific synthesis of 3'-substituted β-L-dideoxynucleosides

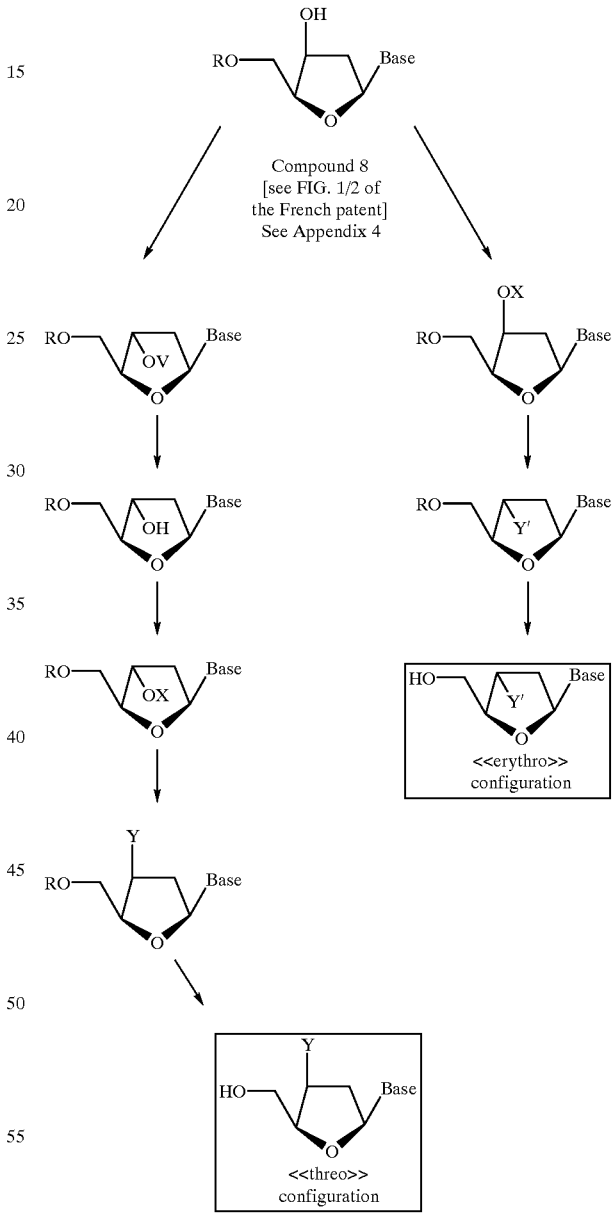

V = acyl ($CH_3$—$\overset{O}{\underset{\|}{C}}$, $C_6H_5$—$\overset{O}{\underset{\|}{C}}$)

X = Leaving group [$CH_3SO_2$, $CH_3C_6H_4SO_2$, $CF_3SO_2$]

Y, Y' = F, $N_3$, $NR_1R_2$[$R_1$, $R_2$ = H, alkyl, aryl], $NO_2$, NOR[R = H, alkyl, acyl], O-alkyl, O-aryl, etc.

EXAMPLE=1-(3-Azido-2-3-dideoxy-β-L-erythro-pentofuranosyl) thymine [β-L-AZT]

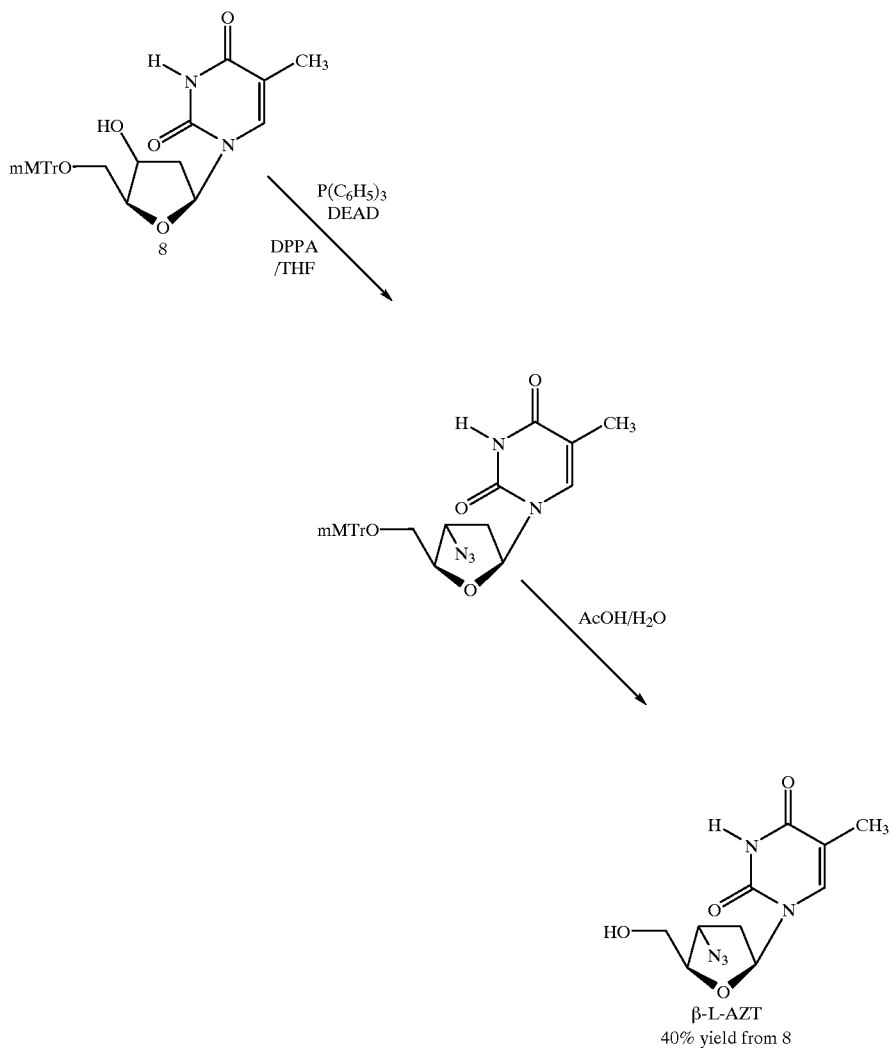

A mixture of diethyl azodicarboxylate (0.46 mL; 2.9 mmol) and diphenyl phosphorazidate (0.62 ml; 2.9 mmol) in TBF (2.9 ml) was added dropwise over 30 min. to a solution of 1-(2-deoxy-5-O-monomethoxytrityl-β-L-threo-pentofuranosyl) thymine [0.5 g, 0.97 mmol] and triphenylphosphine (0.76g, 2.9 mmol) in THF 11.6 ml) at 0° C. The mixture was stirred for 3.5 h at room temperature, and ethanol was added. After concentration to dryness in vacuo, the residue was dissolved in a mixture of acidic acid (240 ml) and water (60 ml) in order to remove the mMTr protecting group. The mixture was stirred for 5 hours at room temperature and was diluted with toluene. The separated aqueous phase was concentrated to dryness in vacuo. The residue was purified over a silica gel column eluted with ethyl acetate to afford β-L-AZT (105 mg, 40%, crystallized from ethyl acetate). The physicochemical data of β-L-AZT were in accordance with literature data [J. Wengel, J-Lau, E. B. Ledersen, C. N. Nielsen, J. Org. Chem. 56 (11), 3591–3594 (1991)].

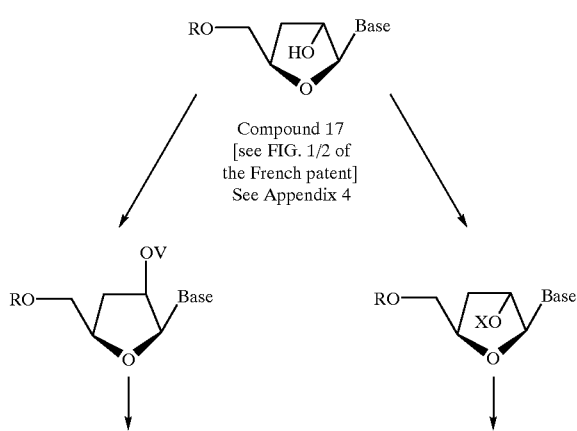

Figure 2:
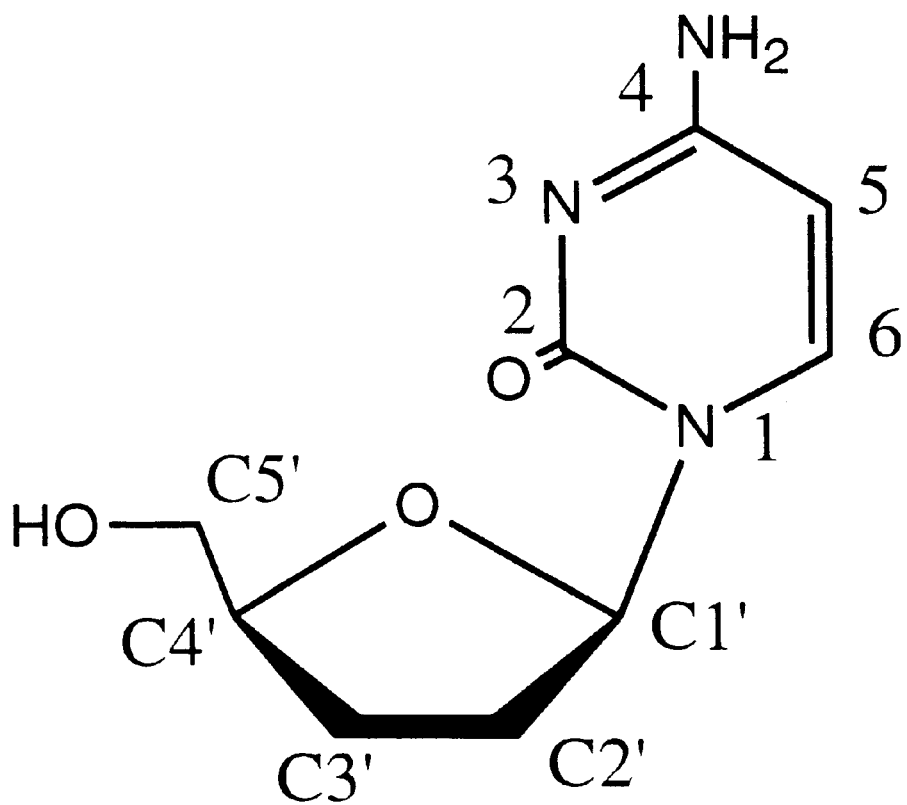
FIG. 2 is an illustration of the numbering scheme used in the chemical nomenclature for nucleosides in this text.

General Scheme for the Stereospecific Synthesis of 2'-substituted β-L-dideoxynucleosides Compound 17
[see FIG. 1/2 of the French patent]
See Appendix 4

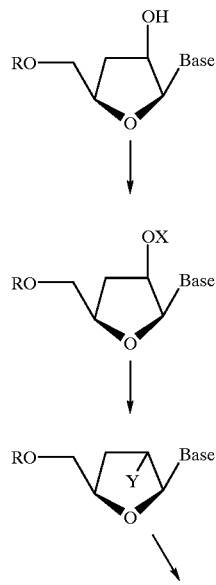
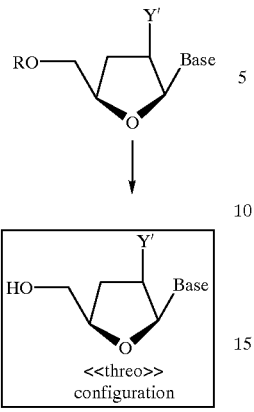
V = acyl [CH₃—C(=O) C₆H₅—C(=O)]
X = Leaving group [CH₃SO₂, CH₃C₆H₄SO₂, H, CF₃SO₂]
Y, Y' = F, N₃, NR₁R₂ [R₁, R₂ = H, alkyl, aryl],
    NO₂, NOR[R = H, alkyl, acyl], O-alkyl, O-aryl, etc.
EXAMPLE=1-(2-Fluoro-2,3-dideoxy-β-L-threo-pentofaranosyl)-5-fluorocytosine [2'-F-β-L β-L-FddC]
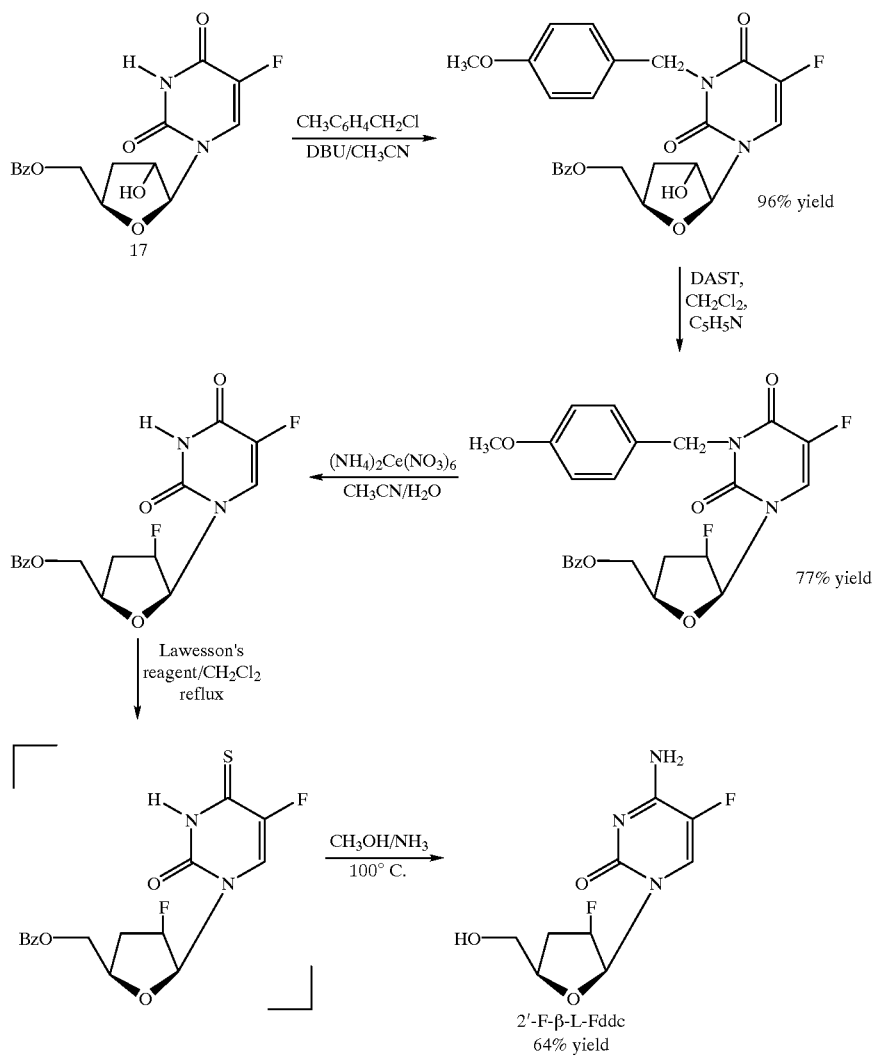

Hitherto unknown 2'-F-β-L-FddC was synthesized in five steps from 1-(5-O-benzoyl3dexoxy-β-L-erythro-pentofuranosyl)-5-fluorouracil 17 with an overall yield of 28%. m.p. 209–210° C. (crystallized from absolute ethanol); UV (Et OH) $\lambda_{max}$ 276$_{nm}$ (ε, 9000), $\lambda_{min}$ 226$_{nm}$ (ε4000), $^{19}$F-NMR (DMSO-d$_6$) δppm: −179.7 (m, F$_2$,), −167.2 (dd, F$_5$; J$_{F,6}$ 7.3 Hz, J$_{F,1'}$=1.5Hz); $^1$H-NMR (DMSO-d$_6$) δppm: 8.30 (d, 1H, H-6; J$_{6,F}$=7.3 Hz), 7.8–7.5 (br S,2H, NH$_2$),5.80 (d, 1H, H-1'J$_{1',F}$=17.4 Hz), 5.34 (t, 1H, OH-5'; J=4.8 Hz), 5.10 (dd, 1H, H-2'; J$_{2',F}$=51.2 Hz; J$_{2',3'}$=3.4 Hz), 4.3 (m, 1H, H-4'), 3.8–3.6 (m, 2H, H-5', 5"), 2.2–2.0 (m, 2H, H-3', H-3"); mass spectra (performed in: glycerol-thioglycerol, 1:1 υ/υ), FAB>0:248 (M+H)$^+$, 130 (BH$_2$)$^+$; FAB<0:246 (M−H)$^-$; [α]$^{20}$$_D$=−16.5 (−c 0.85, DMSO). Anal. Calc. for C$_9$H$_{11}$N$_{3l}$O$_3$F$_2$: C, 43.73; H, 9.49; N. 17.00; F. 15.37. Found: C, 43.56; H, 4.78; N, 16.75; F, 14.96.

Scheme I
Bases = purines or pyrimidines, eventuellement convenablement protegees; R = Benzoyl (Bz)
Acetyl (Ac), monomethoxytrityl (mMTr) or tertiarybutyldiphenylsily (TBDPSI)

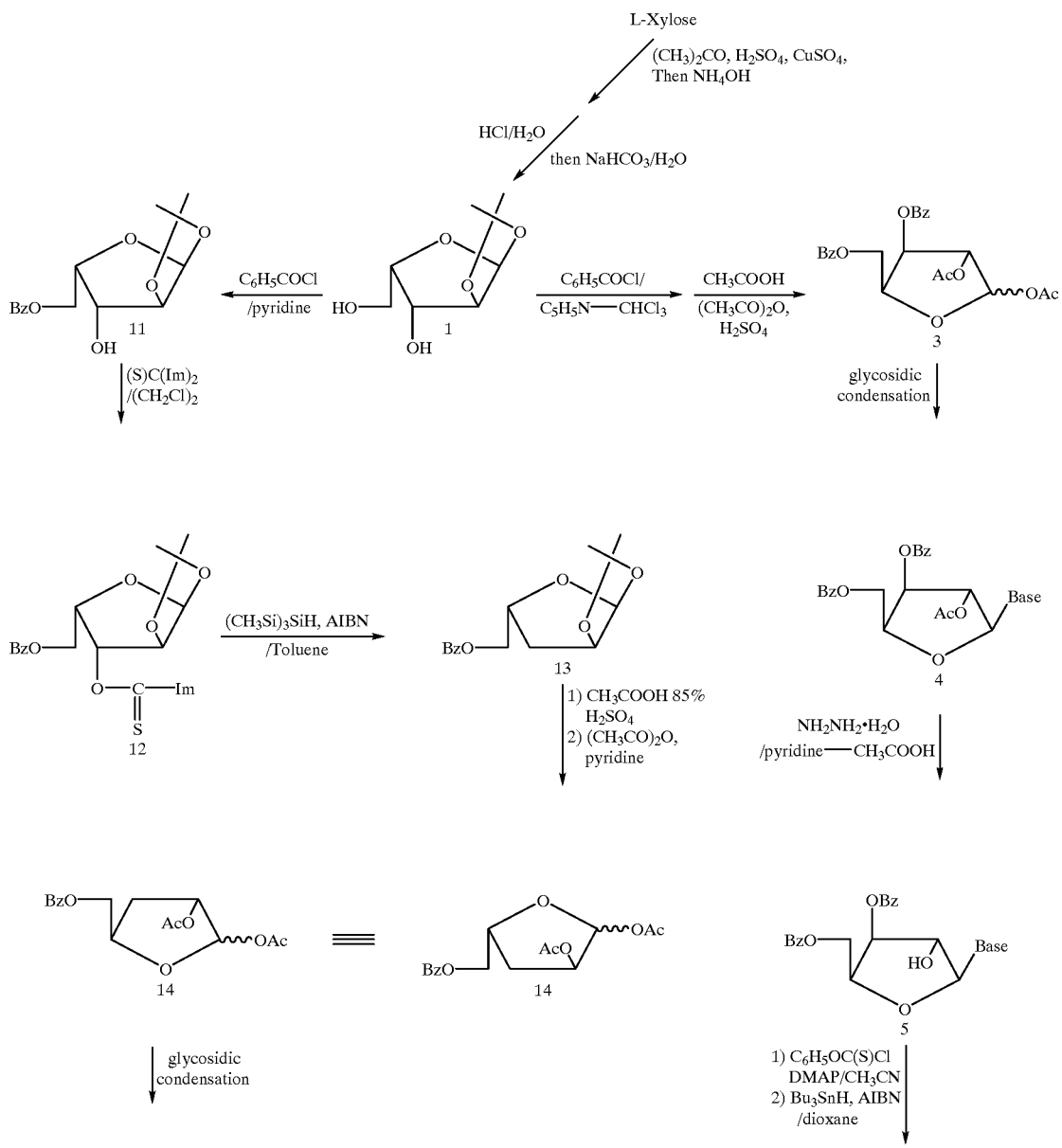

-continued

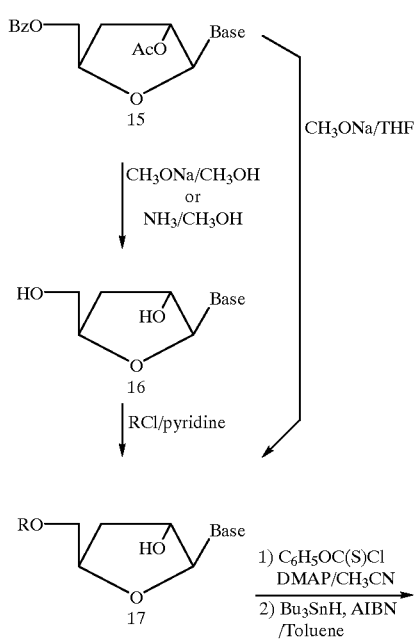
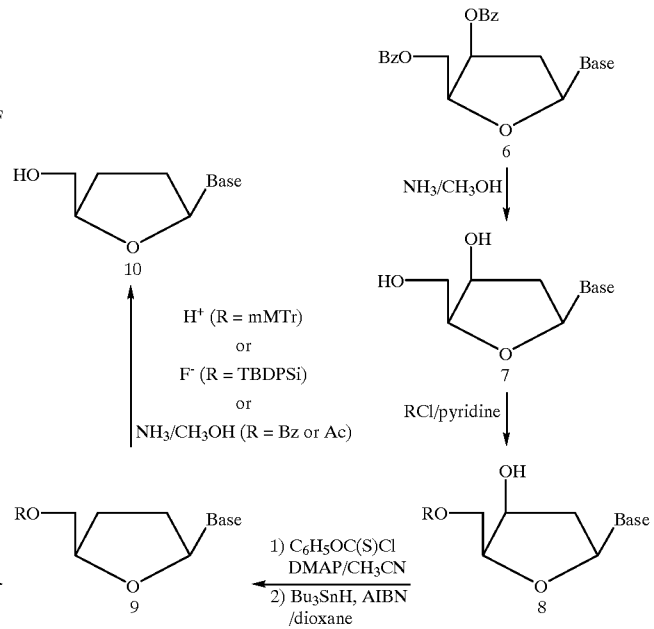

II. Anti-HBV Activity of Nucleosides

The ability of the active compounds to inhibit HBV can be measured by various experimental techniques The assay used herein to evaluate the ability of the disclosed compounds to inhibit the replication of HBV is described in detail in Korba and Gerin, Antiviral Res. 19: 55–70 (1992). For purposes of illustration only, and without limiting the invention, the results of the evaluation of toxicity and anti-HBV activity are provided below for β-L-2', 3"-dideoxycytidine (β-L-FddC), β-L-2', 3'-dideoxy-5-fluorocytidine (βL-ddC), and (+)-β-D-2-hydroxymethyl-5-(5-fluorocytosin-1-yl)-1,3-dioxolane ((+)-β-D-FDOC). The toxicity and anti-HBV activity of (−)-β-L-2-hydroxymethyl-5-(5-fluorocytosin-1-yl)-1,3-oxathiolane ((−)-β-L-FTC) and β-D-2 ', 3'-dideoxycytidine (β-D-ddC) are included as controls. The other compounds disclosed herein can be evaluated similarly.

The samples of β-L-ddC and β-L-5-FddC used in the anti-HBV assays were characterized as follows.

2'. 3'-Dideoxy-β-L-cytidine (β-L-DDC)

m.p. 220–220° C.; UV (EtOH 95) max 273 nm, λmin 252 nm; NMR-$^1$H (DMSO-$d_6$) δppm=7.89 (d. 1H. H-6; J 7.4 Hz). 7.15–6.95 (d large, 2H, NH$_2$), 5.91 (dd. 1H, H1–1'; J=3.0 et 6.5 Hz), 5.66 (d, 1H, H-5; J=7.4 Hz), 4.99 [t. 1H, OH-5'; J–5.2 Hz]. 4.05–3.95 (m, 1H, H-4'), 3.60–3.70 (m, 1H, H-5'; after D$_2$O exchange: dd, 3.64 ppm, J=3.6 et 12.0 Hz). 3.60–3.50 (m. 1H, H-5"; after D$_2$O exchange: dd, 3.50 ppm, J=4,1 et 12.0 Hz), 2.30–2.15 (m. 1H, H-2'), 1.9–1.65 (m. 3H, H-2", 3'et 3"); [a]D 2–103.6 (c 0.8 MeOH); mass spectrum (performed in: glycerol-thioglycerol, 50: 50. v/v); FAB>0 423 [2M+H]$^+$, 304 [M+glycerol+H]$^+$. 212 [M+H]$^+$, 112 [BH$_2$]$^+$, 101 [s]$^+$; FAB<O 210 [M−H]$^-$. Anal. Calc. for C$_9$H$_{13}$N$_3$O$_3$ (M=211.21); C 51.18; H 6.20; N 19.89 found; C 51.34; H 6.25; N 20.12.

2', 3'-Dideoxy-β-L-5-fluoroctidine (β-L-5-FDDC)

m.p.=158–160° C.; UV (EtOH 95) λmax 281 nm (ε, 8100) et 237 nm (ε, 8500); min 260 nm (ε, 5700) et 225 nm (ε, 7800); NMR-$^1$H (DMSO-$d_6$) δppm 8.28 (d. 1H, H-6; J–7.4 Hz), 7.7–7.4 (d large, 2H, NH$_2$), 5.83 (dd poorly resolved, 1H, H-1'), 5.16(t. 1H, OH-5'; J=5.1 Hz), 4.05–3.95 (m, 1H, H-4'), 3.8–3.70 [m, 1H, H 5'; after D2O exchange: dd, 3.71 ppm. J=2.7 et 12.3 Hz], 3.60–3.50 [m. 1H, H-5"; after D$_2$O exchange: dd, 3.52 pm; J=3.3 et 12.3 Hz], 2.35–2.15 (m, 1H, H-2'). 1.95–1.75 (m, 3H, H-2", 3'et 3"): [α]$_D^2$−80.0 (−c 1.0, DMSO); Mass spectrum [performed in: 3-nitrobenzyl alcohol] FAB>0 230 [M+H]$^+$ et 101 [s]$^+$; FAB<O 228 [M−II ]$^-$. Anal. Calculated for C9Hl$_2$N$_3$OF$_3$ (M=229.21); C 47.16; II 5.28; N 18.33, F 8.29, Found. C 16.90; H 5.28; N 18.07; F 8.17.

The antiviral evaluations were performed on two separate passages of cells, two cultures per passage (4 cultures total). All wells, in all plates, were seeded at the same density and at the same time.

Due to the inherent variations in the levels of both intracellular and extracellular HBV DNA, only depressions greater than 3.0-fold (for HBV virion DNA) or 2.5-fold 3J (for HBV DNA replication intermediates) from the average levels for these HBV DNA forms in untreated cells are generally considered to be statistically significant [P<0.05] .Korba and Gerin, Antiviral Res. 19: 55–70, 1992). The levels of integrated HBV DNA in each cellular DNA preparation (which remain constant on a per cell basis in these experiments) were used to calculate the levels of intracellular HBV DNA forms, thereby eliminating technical variations inherent in the blot hybridization assays.

Typical values for extracellular HBV virion DNA in untreated cells range from 50 to 150 pg/ml culture medium (average of approximately 76 pg/ml). Intracellular HBV DNA replication intermediates in untreated cells range from 50 to 100 pg/ug cell DNA (average approximately 74 pglug cell DNA). In general, depressions in the levels of intracellular BBV DNA due to treatment with antiviral compounds are less pronounced, and occur more slowly, than depressions in the levels of HBV virion DNA.

For reference, the manner in which the hybridization analyses were performed for these experiments results in an equivalence of approximately 1.0 pg intracellular HBV DNA/ug cellular DNA to 2–3 genomic copies per cell and 1.0 pg of extracellular HBV DNA/ml culture medium to $3\times10^5$ viral particles/ml.

Toxicity analyses were performed in order to assess whether any observed antiviral effects were due to a general effect on cell viability. The method used was based on the uptake of neutral red dye, a standard and widely used assay for cell viability in a variety of virus-host systems, including HSV (herpes simplex virus) and HIV.

The test compounds were used in the form of 40 mM stock solutions in DMSO (frozen on dry ice). Daily aliquots of the test samples were made and frozen at −20° C. so that each individual aliquot would be subjected to a single freeze-thaw cycle. The daily test aliquots were thawed, suspended into culture medium at room temperature and immediately added to the cell cultures. The compounds were tested at 0.01 to 10 μM for antiviral activity. The compounds were tested for toxicity at concentrations from 1 to 300 μM. The results are provided in Table 1.

observed in untreated cultures) is typically observed in these assays (Korba and Gerin, Antiviral Res. 19: 55–70, 1992).

Example 3

Anti-Hepatitis B Virus Activity

The positive treatment control, β-D-2′,3′-dideoxycytosine [β-D-ddC], induced significant depressions of HBV DNA replication at the concentration used. Previous studies have indicated that at 9–12 μM of β-D-ddC, a 90% depression of HBV RI (relative to average levels in untreated cells) is typically observed in this assay system (Korba and Gerin, Antiviral Res. 19: 55–70, 1992). This is consistent with the data presented in Table 1.

The data presented in Table 1 indicates that all three test compounds ((β-L-FddC), (β-L-ddC), and β-D-FDOC)), were potent inhibitors of HBV replication, causing depression of HBV virion DNA and HBV RI to a degree comparable to, or greater than, that observed following treatment with β-D-ddC.

TABLE 1

EFFECT OF D-DDC, L-DDC, L-FDDC, FDOC and (−)-FTC AGAINST HEPATITIS B VIRUS IN TRANSFECTED HEPG-2 (2.2.15) CELLS

| Compound | HBV viron[a] | | HBV RI[b] | | Cytotoxicity | Selectivity Index $IC_{50}/EC_{90}$ | |
|---|---|---|---|---|---|---|---|
| | $EC_{50} \pm SD$ | $EC_{90} \pm SD$ | $EC_{50} \pm SD$ | $EC_{90} \pm SD$ | $IC_{50} \pm SD$ | Virion | RI |
| β-D-DDC | 1.3 ± 0.2[c] | 2.1 ± 0.3 | 8.1 ± 1.7 | 12.0 ± 2.4 | 219 ± 28[c] | 104 | 18 |
| | 1.5 ± 0.7 | 9.4 ± 2.5 | 3.2 ± 0.6 | 11.0 ± 2.0 | 216 ± 22 | 23 | 20 |
| β-L-DDC | 0.033 ± 0.003 | 1.1 ± 0.2 | 0.107 ± 0.012 | 1.8 ± 0.2 | 493 ± 64 | 448 | 274 |
| β-L-FDDC | 0.12 ± 0.01 | 0.30 ± 0.03 | 2.8 ± 0.4 | 4.8 ± 0.6 | 438 ± 57 | 1,460 | 91 |
| (+)-β-D-FDOC | 0.020 ± 0.003 | 0.195 ± 0.027 | 0.062 ± 0.012 | 0.23 ± 0.02 | 251 ± 23 | 1,287 | 1,091 |
| (−)-β-L-FTC | 0.017 ± 0.005 | 0.15 ± 0.02 | 0.049 ± 0.008 | 0.18 ± 0.03 | 292 ± 13 | 1,947 | 1,622 |

[a]Extracellular DNA
[b]Replicative intermediates (Intracellular DNA)
[c]μM

Example 2

Toxicity of Compounds

The ability of the active compounds to inhibit the growth of virus in 2.2.15 cell cultures (HepG$^2$ cells transformed with hepatitis virion) was evaluated. As illustrated in Table 1, no significant toxicity (greater than 50% depression of the dye uptake levels observed in untreated cells) was observed for any of the test compounds at the concentrations 100 μM. The compounds were moderately toxic at 300 μM, however, all three compounds exhibited less toxicity at this concentration than β-D-ddC. It appears that the $IC_{50}$ of β-L-ddC and β-L-FddC is approximately twice that of β-D-ddC.

Toxicity analyses were performed in 96-well flat bottomed tissue culture plates. Cells for the toxicity analyses were cultured and treated with test compounds with the same schedule as used for the antiviral evaluations. Each compound was tested at 4 concentrations, each in triplicate cultures. Uptake of neutral red dye was used to determine the relative level of toxicity. The absorbance of internalized dye at 510 nM ($A_{510}$) was used for the quantitative analysis. Values are presented as a percentage of the average $A_{510}$ values (±standard deviations) in 9 separate cultures of untreated cells maintained on the same 96-well plate as the test compounds. The percentage of dye uptake in the 9 control cultures on plate 40 was 100±3. At 150–190 μM β-D-ddC, a 2-fold reduction in dye uptake (versus the levels Example 4

The effect of selected β-L-derivatives against Hepatitis B virus replication in transfected Hep G-2 cells is described in Table 4.

TABLE 1

Effect of L-derivatives against Hepatitis B virus replication in transfected Hep G-2 (2.2.15) cells.

| Compound | HBV Virion[a] | HBV RI[b] | Cytotoxicity | Selectivity Index $IC_{50}/EC_{50}$ | |
|---|---|---|---|---|---|
| | $EC_{50}$ | $EC_{50}$ | $IC_{50}$ | Virion | RI |
| β-L-ddA | 5.0[c] | 5.0 | 250 | 50 | 50 |
| Bis (Sate) β-L-ddAMP | 0.45 | 0.35 | 200 | 445 | 571 |
| β-L-AZT | >10 | >10 | 1000 | NA | NA |
| Bis (Sate) β-L-AZTMP | 7.5 | 8 | 200 | 27 | 25 |
| 2′-F-β-L-5FDDC | 1.7 | 5.0 | 210 | 124 | 42 |

[a]Extracellular DNA
[b]Replicative intermediates (Intracellular DNA)
[c]μM

Example 5

The Comparative inhibitory effect of selected triphosphates on woodchuck hepatitis virus DNA polymerase is set out in Table 5.

TABLE 2

Comparative inhibitory activities of L-nucleoside triphosphates on woochuck hepatitis virus DNA polymerase and human DNA polymerase α and β.

| Inhibitor | WHB DNA Pol IC$_{50}$ ($\mu$M) | DNA Pol α Ki ($\mu$M) | DNA Pol β Ki ($\mu$M) |
|---|---|---|---|
| β-L-AZTPP | 0.2 | >100 | >100 |
| βL-ddATP | 2.1 | >100 | >100 |
| 3-TC-TP | 1.0 | >100 | >100 |
| β-L-5FDDCTP | 2.0 | >100 | >100 |

III. Preparation of Pharmaceutical Compositions

The compounds disclosed herein and their pharmaceutically acceptable salts, prodrugs, and derivatives, are useful in the prevention and treatment of HBV infections and other related conditions such as anti-HBV antibody positive and HBV-positive conditions, chronic liver inflammation caused by HBV, cirrhosis, acute hepatitis, fulminate hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

Humans suffering from any of these conditions can be treated by administering to the patient an effective HBV-treatment amount of one or a mixture of the active compounds described herein or a pharmaceutically acceptable derivative or salt thereof, optionally in a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount without causing serious toxic effects in the patient treated.

A preferred dose of the active compound for all of the above-mentioned conditions will be in the range from about 1 to 60 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art. In one embodiment, the active compound is administered as described in the product insert or Physician's Desk Reference for 3'-azido-3'-deoxythymidine (AZT), 2', 3'-dideoxyinosine (DDI), 2', 3'-dideoxycytidine (DDC), or 2', 3'-dideoxy-2',3'-didehydrothymidine (D4T) for HIV indication.

The compound is conveniently administered in unit any suitable dosage form, including but not limited to one containing 7 to 3000 mg, preferably 70 to 1400 mg of active ingredient per unit dosage form. A oral dosage of 50–1 000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The active compound can be provided in the form of pharmaceutically acceptable salts. As used herein, the term pharmaceutically acceptable salts or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, amnnonium, or ethylenediamine; or (c) combinations of (a) and (b); e.g., a zinc tannate salt or the like.

Modifications of the active compound, specifically at the $N^6$ or $N^4$ and 5'-O positions, can affect the bioavailability and rate of metabolism of the active species, thus providing control over the delivery of the active species.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound, or pharmaceutically acceptable derivative or salt thereof can also be mixed with other active materials that do not impair the desired action, or with materials that supplement the desired action, such as antibiotics, antifungals, antiinflammatories, or other antivirals, including anti-HBV, anti-cytomegalovirus, or anti-HIV agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS). In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of the appended claims.

We claim:

1. A method for treating a patient infected with hepatitis B comprising administering an effective amount of a nucleotide prodrug of β-L-2', 3'-dideoxyadenosine to the infected patient, and wherein the prodrug component of the nucleotide provides controlled delivery of the active species.

2. The method of claim 1, wherein the nucleotide is a monophosphate.

3. The method of claim 1, wherein the nucleotide is a diphosphate.

4. The method of claim 1, wherein the nucleotide is a triphosphate.

5. The method of claim 1, wherein the nucleotide prodrug is an alkylated nucleotide.

6. The method of claim 1, wherein the nucleotide prodrug is an acylated nucleotide.

7. The method of claim 1, wherein the nucleotide prodrug is a lipophilic derivative of the nucleotide.

8. The method of claim 1, wherein the nucleotide prodrug is a derivative in which one or more hydrogens in the phosphate moiety of the nucleotide is replaced by alkyl.

9. The method of claim 1, wherein the nucleotide prodrug is a derivative in which one or more hydrogens in the phosphate moiety of the nucleotide is replaced by a steroid.

10. The method of claim 1, wherein the nucleotide prodrug is a derivative in which one or or more hydrogens in the phosphate moiety of the nucleotide is replaced by a carbohydrate.

11. The method of claim 1, wherein the nucleotide prodrug is a derivative in which one or more hydrogens in the phosphate moiety of the nucleotide is replaced by a sugar.

12. The method of claim 1, wherein the nucleotide prodrug is a derivative in which one or more hydrogens in the phosphate moiety of the nucleotide is replaced by a 1,2-diacylglycerol.

13. The method of claim 1, wherein the nucleotide prodrug is a derivative in which one or more hydrogens in the phosphate moiety of the nucleotide is replaced by an alcohol.

14. A method for treating a patient infected with hepatitis B comprising administering an effective amount of a nucleotide prodrug of the nucleoside βL-2', 3'-dideoxyadenosine the infected patient, and wherein the prodrug component of the nucleotide increases the activity of the nucleoside in vivo.

15. A nucleotide prodrug of the nucleoside β-L-2', 3'-dideoxyadenosine, wherein the prodrug component of the nucleotide stabilizes the phosphate in vivo, and provides controlled delivery of the active species.

16. A pharmaceutical composition comprising an effective amount of a nucleotide prodrug of the nucleoside β-L-2', 3'-dideoxyadenosine, wherein the prodrug component of the nucleotide stabilizes the phosphate in vivo, and provides controlled delivery of the active species, in combination with a pharmaceutically acceptable carrier.

* * * * *